United States Patent
Chi et al.

(10) Patent No.: US 10,396,298 B2
(45) Date of Patent: Aug. 27, 2019

(54) IRIDIUM COMPLEX AND ORGANIC LIGHT-EMITTING DIODE USING THE SAME

(71) Applicant: National Tsing Hua University, Hsinchu (TW)

(72) Inventors: Yun Chi, Hsinchu (TW); Rajakannu Palanisamy, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 333 days.

(21) Appl. No.: 15/415,691

(22) Filed: Jan. 25, 2017

(65) Prior Publication Data

US 2018/0212161 A1  Jul. 26, 2018

(51) Int. Cl.
| H01L 51/00 | (2006.01) |
| C07F 15/00 | (2006.01) |
| C09K 11/06 | (2006.01) |
| H01L 51/50 | (2006.01) |

(52) U.S. Cl.
CPC ...... H01L 51/0085 (2013.01); C07F 15/0033 (2013.01); C09K 11/06 (2013.01); H01L 51/009 (2013.01); C09K 2211/1007 (2013.01); C09K 2211/1029 (2013.01); C09K 2211/1044 (2013.01); C09K 2211/185 (2013.01); H01L 51/5016 (2013.01)

(58) Field of Classification Search
CPC ............... H01L 51/0085; H01L 51/009; H01L 51/5016; C09K 11/06; C09K 2211/1007; C09K 2211/1044; C09K 2211/1029; C09K 2211/185; C07F 15/0033
See application file for complete search history.

(56) References Cited

U.S. PATENT DOCUMENTS

| 5,929,265 A * | 7/1999 | Dorta | C07F 15/004 548/490 |
| 8,883,322 B2 | 11/2014 | Wu et al. | |
| 2004/0247934 A1* | 12/2004 | Takeuchi | H01L 51/004 428/690 |
| 2010/0034733 A1* | 2/2010 | Fukuzumi | B01J 31/1815 423/658.2 |
| 2012/0228583 A1* | 9/2012 | Wu | H01L 51/0085 257/40 |

FOREIGN PATENT DOCUMENTS

| CN | 102977150 | 3/2013 |
| TW | 200601888 | 1/2006 |
| TW | 201437327 | 10/2014 |
| TW | 201612187 | 4/2016 |
| TW | 201643174 | 12/2016 |

OTHER PUBLICATIONS

"Office Action of Taiwan Counterpart Application", dated Jun. 6, 2018, p. 1-p. 4.
Kuei et al., "Bis-Tridentate Ir(III) Complexes with Nearly Unitary RGB Phosphorescence and Organic Light-Emitting Diodes with External Quantum Effi ciency Exceeding 31%", Adv. Mater. 19, Feb. 2016, 2795-2800.
Lin et al., "Bis-Tridentate Iridium(III) Phosphors Bearing Functional 2-Phenyl-6-(imidazol-2-ylidene) pyridine and 2-(Pyrazol-3-yl)-6-phenylpyridine Chelates for Efficient OLEDs", Organometallics, Jun. 2016, pp. 1813-1824.

* cited by examiner

*Primary Examiner* — Alexander C Kollias
(74) *Attorney, Agent, or Firm* — J.C. Patents

(57) ABSTRACT

An iridium complex and an OLED using the same are provided. The iridium complex is represented by general formula (I). In the general formula (I), A1, A2, A3, A4 and A5 are each independently a 5-membered unsaturated ring or a 6-membered unsaturated ring.

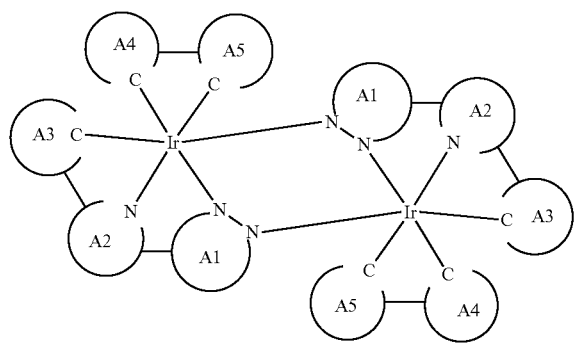

7 Claims, 3 Drawing Sheets

IRIDIUM COMPLEX AND ORGANIC LIGHT-EMITTING DIODE USING THE SAME

BACKGROUND OF THE INVENTION

1. Field of the Invention

The invention relates to a metal complex, and more particularly, to an iridium complex and an application thereof.

2. Description of Related Art

Organic-light emitting diode (OLED) devices have received much attention in the display and solid state lighting industry, especially in the flat panel display industry, since the OLED devices can be operated under low driving voltage and can produce high luminous efficiency.

To develop a flat panel display with full colour, the development of a coloured light-emitting material that is easy to synthesize and has high luminous efficiency is the main object of current OLED research. The existing iridium complex has suitable emission efficiencies, but the rigidity, stability, emission wavelength and ease of synthesis thereof are insufficient.

SUMMARY OF THE INVENTION

The invention provides an iridium complex that has sufficient rigidity and stability and is easy to synthesize, and the emission wavelength of the complex is easily tuned by varying substituent(s) on the tridentate ligand.

The invention also provides an iridium complex represented by general formula (I):

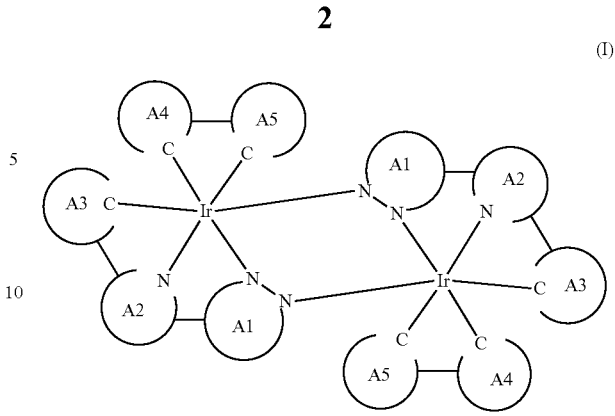

(I)

wherein A1, A2, A3, A4 and A5 are each independently a 5-membered unsaturated ring or a 6-membered unsaturated ring.

In an embodiment of the invention, the iridium complex of the invention is represented by general formula (IA):

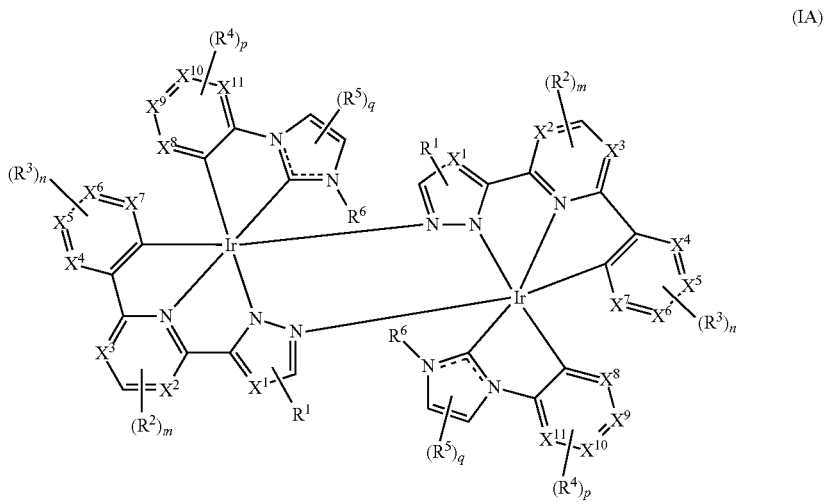

(IA)

wherein each $X^1$ to $X^{11}$ are each independently carbon or nitrogen; each $R^1$ is independently hydrogen, substituted or unsubstituted $C_1$-$C_{12}$ alkyl, substituted or unsubstituted $C_6$-$C_{12}$ aryl, or —$C_fF_{2f+1}$, and f is an integer of 0 to 3; each $R^2$, each $R^3$ and each $R^4$ are independently hydrogen, substituted or unsubstituted $C_1$-$C_{12}$ alkyl, substituted or unsubstituted $C_1$-$C_6$ alkoxyl, substituted or unsubstituted $C_6$-$C_{12}$ aryl, or —$C_fF_{2f+1}$, and f is an integer of 0 to 3; m is an integer of 0 to 3; n is an integer of 0 to 4; p is an integer of 0 to 4; each $R^5$ is independently hydrogen, substituted or unsubstituted $C_1$-$C_{12}$ alkyl, or substituted or unsubstituted $C_1$-$C_6$ alkoxy; q is an integer of 1 to 2; each $R^6$ is independently hydrogen, substituted or unsubstituted $C_1$-$C_{12}$ alkyl, or substituted or unsubstituted $C_6$-$C_{12}$ aryl; when m is equal to or greater than 2, two or more $R^2$'s can joint to form a $C_3$-$C_8$ aromatic ring; when n is equal to or greater than 2, two or more $R^3$'s can joint to form a $C_3$-$C_8$ aromatic ring; when p is equal to or greater than 2, two or more $R^4$'s can joint to form a $C_3$-$C_8$ aromatic ring; and when q is equal to or greater than 2, two or more $R^5$'s can joint to form a $C_3$-$C_8$ aromatic ring.

The invention also provides an organic light-emitting diode that includes two electrodes and a light-emitting layer disposed between the two electrodes, wherein the light-emitting layer contains the above-mentioned iridium complex.

In view of the above, the iridium complex of the invention has strong rigidity and high stability, and the luminous efficiency thereof is accordingly increased. Furthermore, the iridium complex of the invention can be synthesized from an iridium precursor, a chelating tridentate and a bidentate carbene ligand by a one-step process rather than complicated process steps. Moreover, the emission wavelength of the iridium complex can be easily adjusted by varying the substituent(s) on the tridentate ligand(s) and/or bidentate carbene ligand(s). Therefore, wide range of emission wavelength of the iridium complex can be achieved, so the application of the iridium complex of the invention is very broad.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
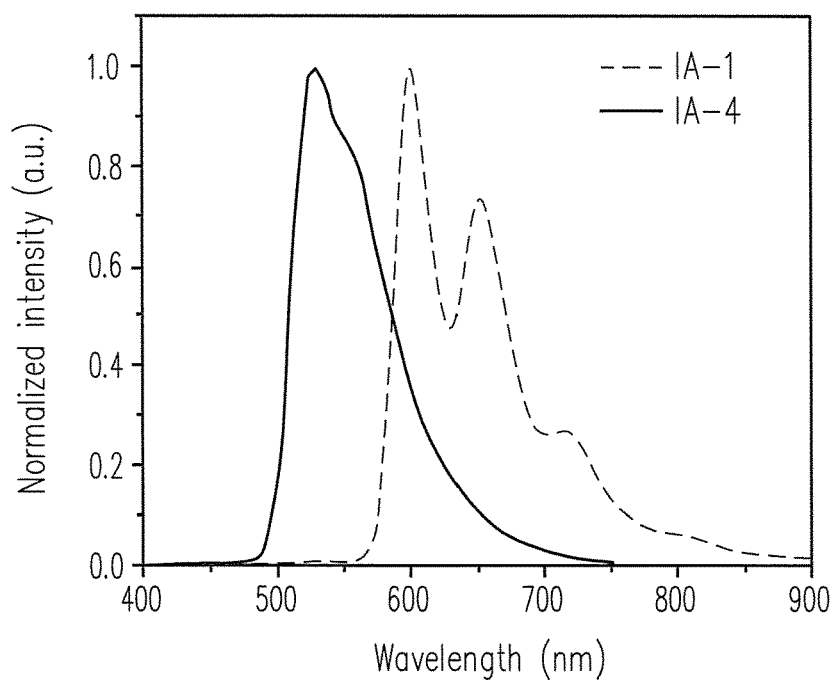
FIG. 1 shows the emission spectrum of each of compounds (IA-1) and (IA-4).

Reference will now be made in detail to the present preferred embodiments of the invention, examples of which are illustrated in the accompanying drawings. Wherever possible, the same reference numbers are used in the drawings and the description to refer to the same or like parts.

The iridium complex of the invention is represented by general formula (I):

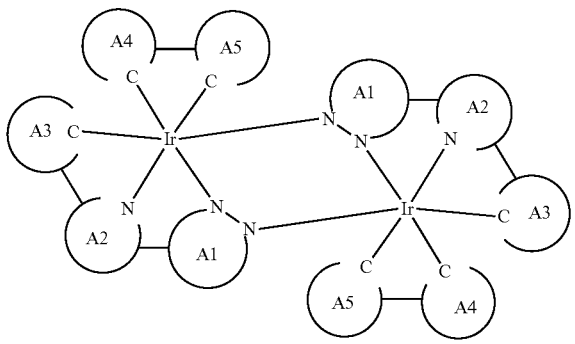

(I)

wherein A1, A2, A3, A4 and A5 are each independently a 5-membered unsaturated ring or a 6-membered unsaturated ring.

Specifically, A1, A2 and A3 fragments form a dianionic tridentate chelating ligand (A1-A2-A3), while A4 and A5 join to constitute another monoanionic bidentate chelating ligand (A4-A5). These tridentate and bidentate chelates are coordinated to an iridium metal atom, forming a penta-coordinated iridium complex fragment [Ir(A1-A2-A3)(A4-A5)], shown on the left side of formula (I). The A1 fragment contains two adjacent nitrogen atoms, among which the inner nitrogen atom is coordinated to the same iridium atom that is encapsulated by the previously mentioned tridentate (A1-A2-A3) and bidentate (A4-A5) chelates. In contrast, the outer nitrogen atom of the A1 fragment is coordinated to the sixth coordination site of the second, identical penta-coordinated iridium complex fragment [Ir(A1-A2-A3)(A4-A5)], shown on the right side of formula (I). In such a way, the iridium complex of the invention has a dimeric molecular structure [Ir(A1-A2-A3)(A4-A5)]$_2$. In some embodiments, the iridium complex of the invention is called a dinuclear Ir(III) complex.

In an embodiment, each A1 is a 5-membered or 6-membered unsaturated ring containing 2 or 3 nitrogen atoms and 0 oxygen or sulphur atom; each A2 is a 5-membered or 6-membered unsaturated ring containing 1, 2 or 3 nitrogen atoms and 0 oxygen or sulphur atom; each A3 and A4 is independently a 5-membered or 6-membered unsaturated ring containing 0, 1, 2, 3 or 4 nitrogen atoms and 0 oxygen or sulphur atom; and each A5 is a 5-membered or 6-membered unsaturated ring containing 2 nitrogen atoms and 0 oxygen or sulphur atom.

In an embodiment, A1, A2, A3, A4 and A5 on the left side of formula (I) are respectively identical to A1, A2, A3, A4 and A5 on the right side of formula (I). Specifically, the iridium complex of the invention has a symmetric structure, in which the ring structures and substituent(s) thereof on the left side of formula (I) are respectively identical to the ring structures and substituent(s) thereof on the right side of formula (I).

In an embodiment, at least one of A1, A2, A3, A4 and A5 on the left side of formula (I) is different from the corresponding A1, A2, A3, A4 and A5 on the right side of formula (I). Specifically, the iridium complex of the invention has an asymmetric structure, in which the ring structures and/or substituent(s) thereof on the left side of formula (I) are not exactly the same as the ring structures and/or substituent(s) thereof on the right side of formula (I).

In an embodiment, when the iridium complex of the invention has an asymmetric structure, at least one of the following cases is satisfied:

a case in which A1 on the left side of formula (I) is different from A1 on the right side of formula (I);

a case in which A2 on the left side of formula (I) is different from A2 on the right side of formula (I);

a case in which A3 on the left side of formula (I) is different from A3 on the right side of formula (I);

a case in which A4 on the left side of formula (I) is different from A4 on the right side of formula (I); and a case in which A5 on the left side of formula (I) is different from A5 on the right side of formula (I).

In an embodiment, at least one substituent on A1, A2, A3, A4 and A5 on a left side of formula (I) is different from a substituent at the corresponding position on the corresponding A1, A2, A3, A4 and A5 on a right side of formula (I). Specifically, the iridium complex of the invention has an asymmetric structure, in which the ring structures on the left side of formula (I) are the same as the ring structures on the right side of formula (I), while the substituent(s) of the ring structures on the left side of formula (I) is different from the substituent(s) of the ring structures on the right side of formula (I).

In an embodiment, when the iridium complex of the invention has an asymmetric structure, at least one of the following cases is satisfied:

a case in which a substituent on the A1 on the left side of formula (I) is different from a substituent at the corresponding position on the A1 on a right side of formula (I);

a case in which a substituent on the A2 on the left side of formula (I) is different from a substituent at the corresponding position on the A2 on a right side of formula (I);

a case in which a substituent on the A3 on the left side of formula (I) is different from a substituent at the corresponding position on the A3 on a right side of formula (I);

a case in which a substituent on the A4 on the left side of formula (I) is different from a substituent at the corresponding position on the A4 on a right side of formula (I); and a case in which a substituent on the A5 on the left side of formula (I) is different from a substituent at the corresponding position on the A5 on a right side of formula (I).

In an embodiment, the iridium complex of the invention is represented by general formula (IA):

wherein each $X^1$ to $X^{11}$ are each independently carbon or nitrogen; each $R^1$ is independently hydrogen, substituted or unsubstituted $C_1$-$C_{12}$ alkyl, substituted or unsubstituted $C_6$-$C_{12}$ aryl, or —$C_fF_{2f+1}$, and f is an integer of 0 to 3; each $R^2$, each $R^3$ and each $R^4$ are independently hydrogen, substituted or unsubstituted $C_1$-$C_{12}$ alkyl, substituted or unsubstituted $C_1$-$C_6$ alkoxyl, substituted or unsubstituted $C_6$-$C_{12}$ aryl, or —$C_fF_{2f+1}$, and f is an integer of 0 to 3; m is an integer of 0 to 3; n is an integer of 0 to 4; p is an integer of 0 to 4; each $R^5$ is independently hydrogen, substituted or unsubstituted $C_1$-$C_{12}$ alkyl, or substituted or unsubstituted $C_1$-$C_6$ alkoxy; q is an integer of 1 to 2; each $R^6$ is independently hydrogen, substituted or unsubstituted $C_1$-$C_{12}$ alkyl, or substituted or unsubstituted $C_6$-$C_{12}$ aryl; when m is equal to or greater than 2, two or more $R^2$'s can joint to form a $C_3$-$C_8$ aromatic ring; when n is equal to or greater than 2, two or more $R^3$'s can joint to form a $C_3$-$C_8$ aromatic ring; when p is equal to or greater than 2, two or more $R^4$'s can joint to form a $C_3$-$C_8$ aromatic ring; and when q is equal to or greater than 2, two or more $R^5$'s can joint to form a $C_3$-$C_8$ aromatic ring.

In the general formula (IA), each $X^1$ can be the same or different; each $X^2$ can be the same or different; each $X^3$ can be the same or different; each $X^4$ can be the same or different; each $X^5$ can be the same or different; each $X^6$ can be the same or different; each $X^7$ can be the same or different; each $X^8$ can be the same or different; each $X^9$ can be the same or different; each $X^{10}$ can be the same or different; each $X^{11}$ can be the same or different; each $R^1$ can be the same or different; each $R^2$ can be the same or different; each $R^3$ can be the same or different; each $R^4$ can be the same or different; each $R^5$ can be the same or different; and each $R^6$ can be the same or different.

Specifically, the iridium complex of the invention has one carbene fragment coordinated to each of the individual iridium metal. The carbene fragments can increase the energy level of metal centred d-d excited state of the central iridium atom, thus increasing the luminous efficiency of the iridium complex.

In addition, the emission wavelength of the iridium complex of the invention can be easily adjusted by varying the substituent(s) on the ring structure(s). Specifically, the substituent(s) on the tridentate ligand(s) and/or bidentate carbene ligand(s) can be easily adjusted, so the emission colour

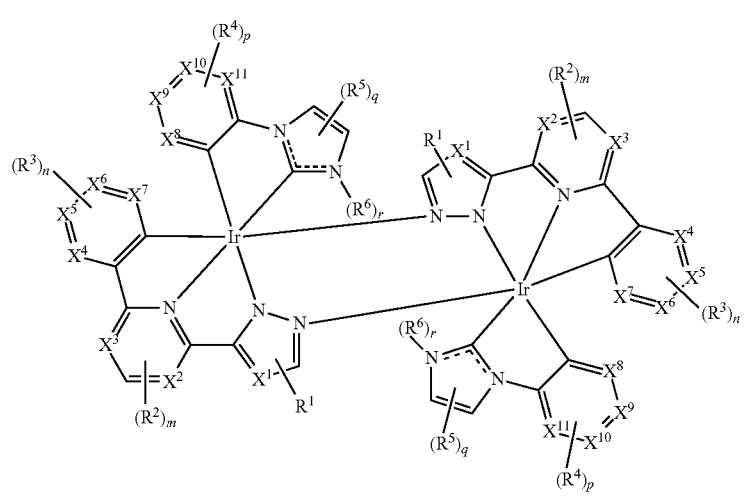

(IA)

of the iridium complex can be easily tuned from red, yellow, green and even to blue by varying the substituent(s) on the ligand(s). Therefore, wide range of emission wavelength of the iridium complex can be easily achieved.

The above-mentioned 5-membered or 6-membered unsaturated ring or aromatic ring can include an aromatic hydrocarbon ring or an aromatic heterocyclic ring. Specific examples of the aromatic ring include a phenyl ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring.

In an embodiment, each $R^1$ is $-C_fF_{2f+1}$, and f is an integer of 0 to 3.

In an embodiment, the iridium complex of the invention has a structure represented by one of formula (IA-1) to formula (IA-50):

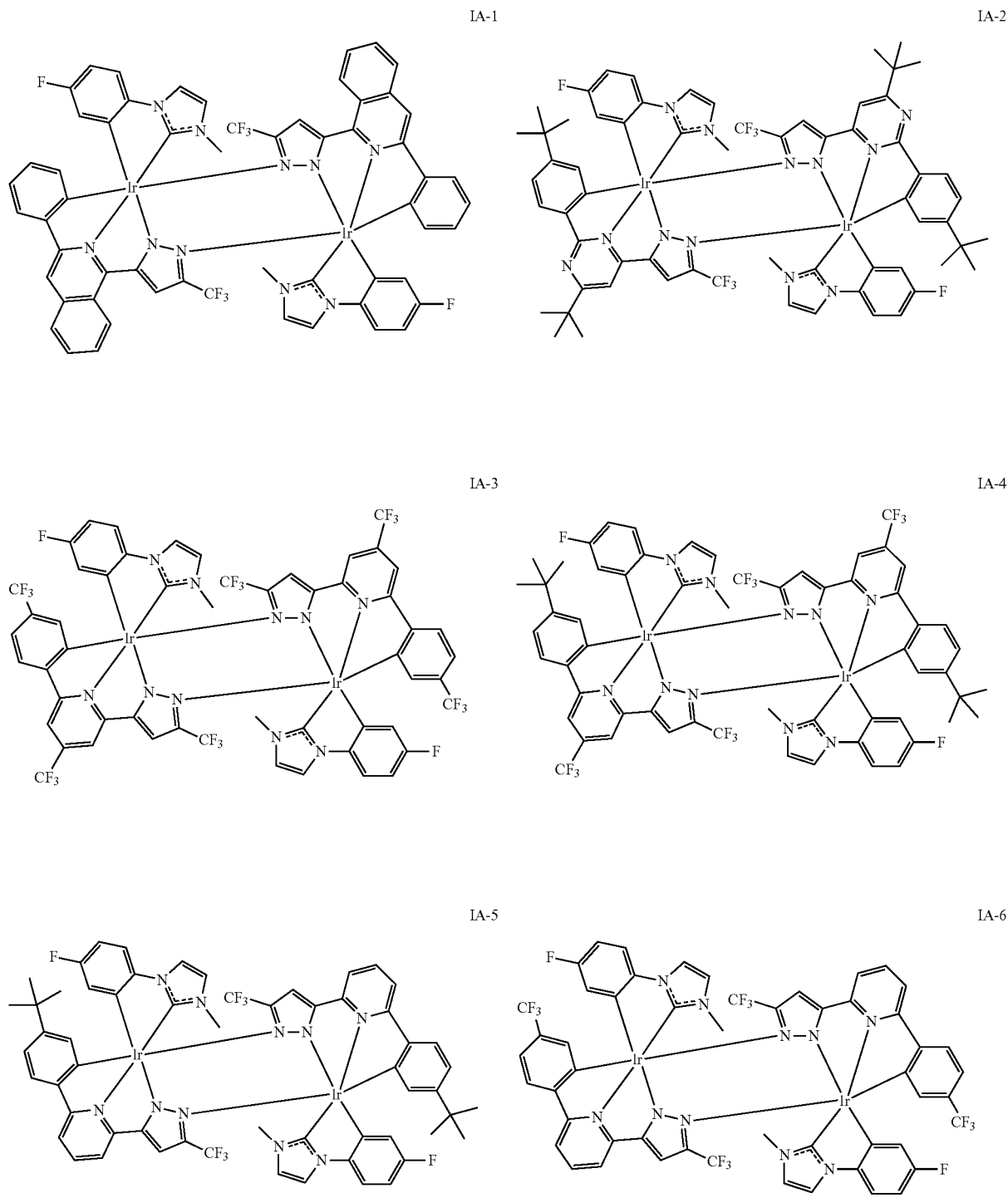

-continued
IA-7
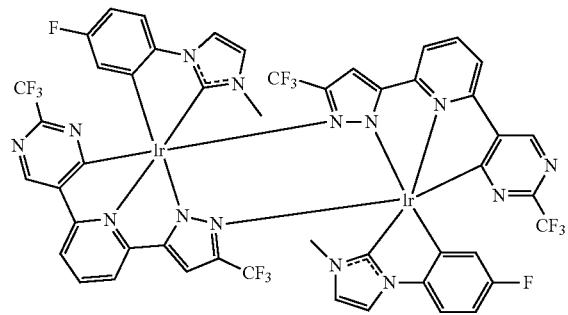
IA-8
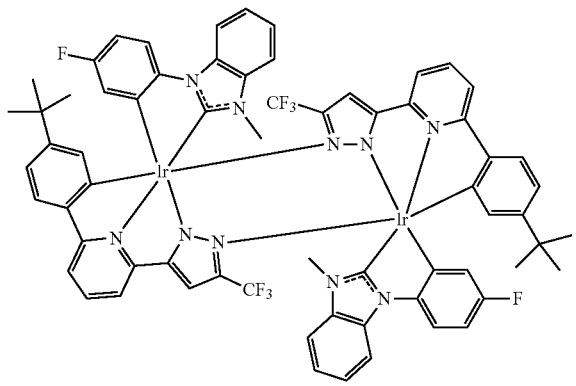
IA-9
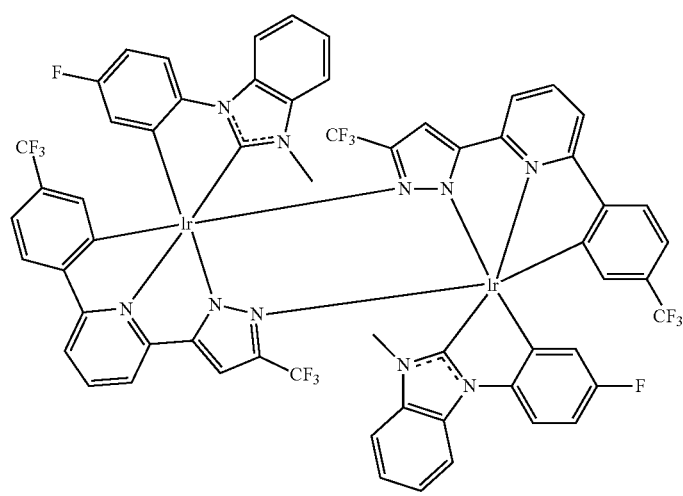
IA-10
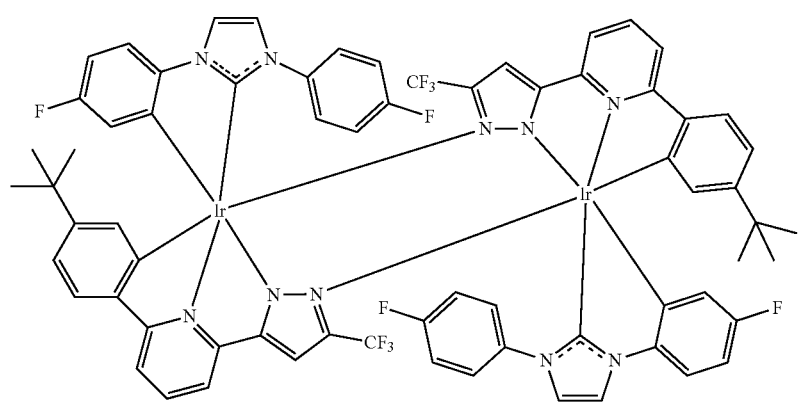

-continued
IA-11
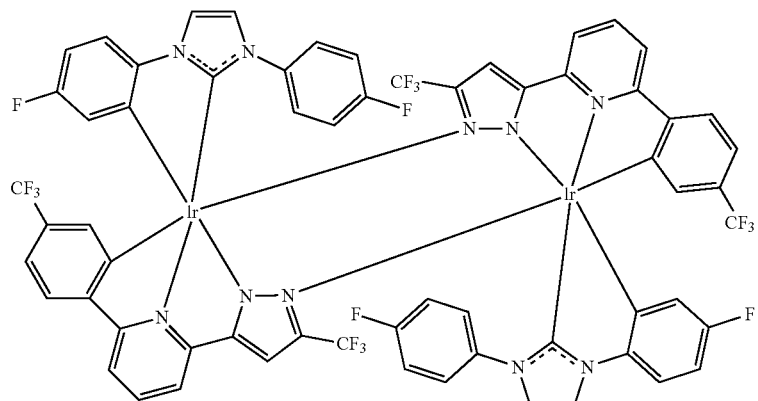
IA-12
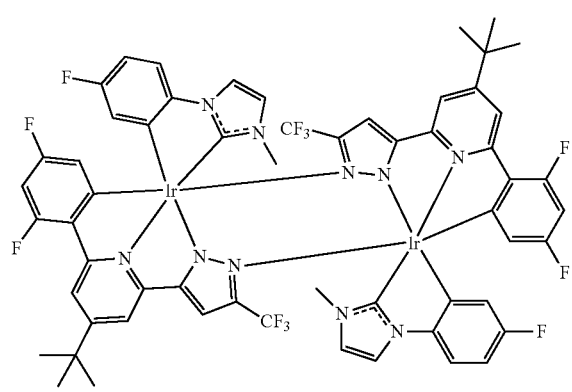
IA-13
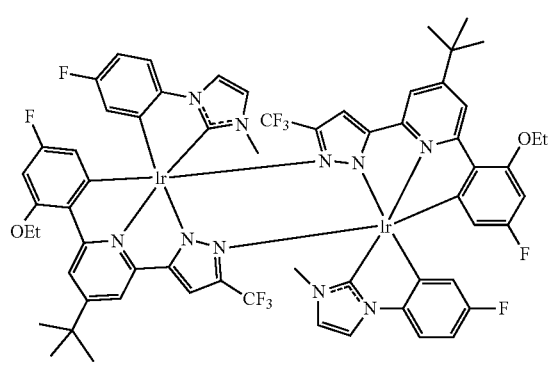
IA-14
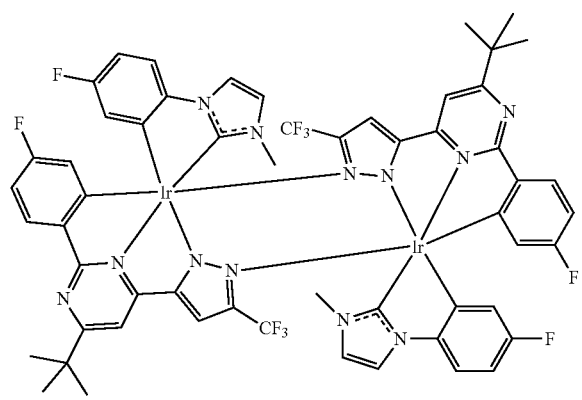
IA-15
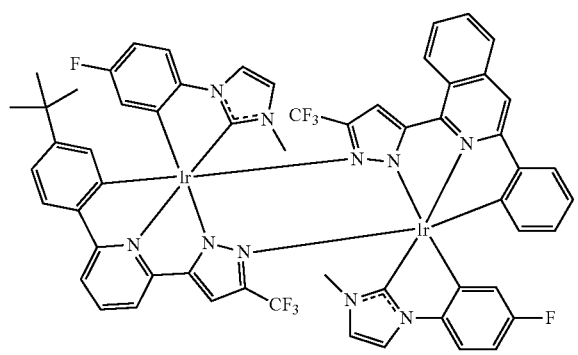
IA-16
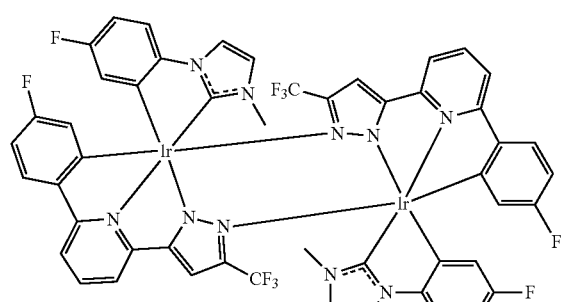
IA-17
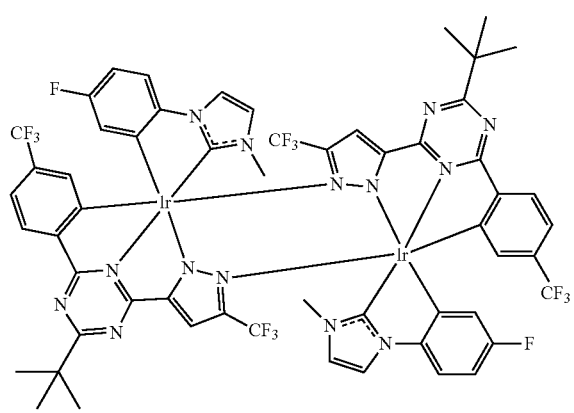

-continued
IA-18
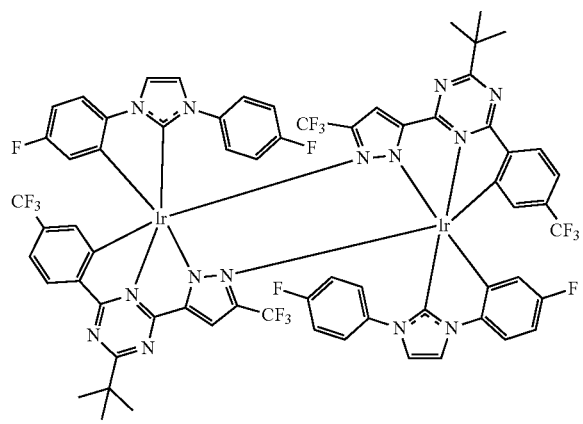
IA-19
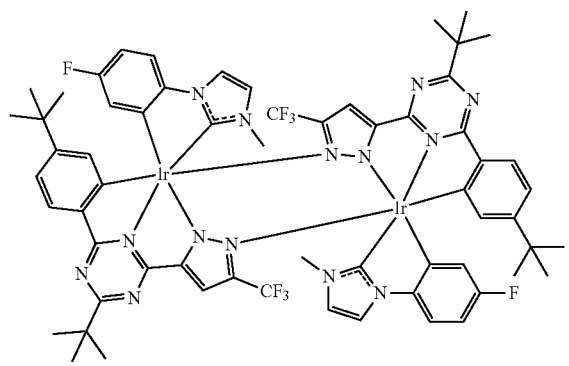
IA-20
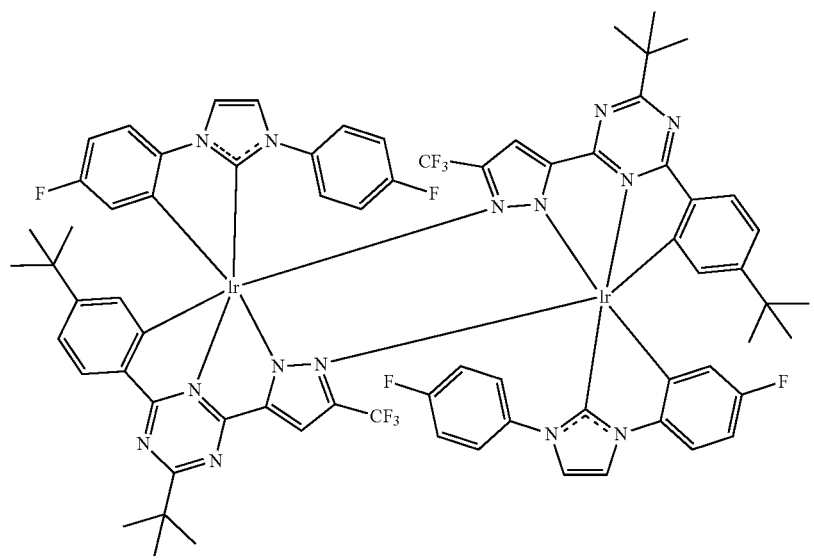
IA-21
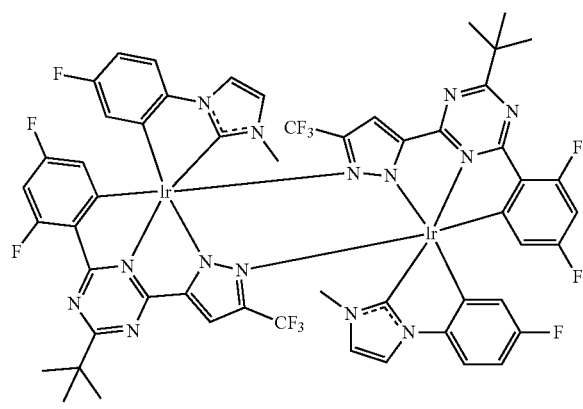
IA-22
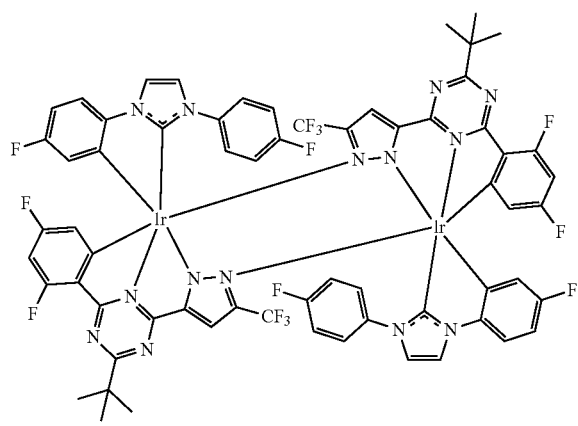

-continued
IA-23
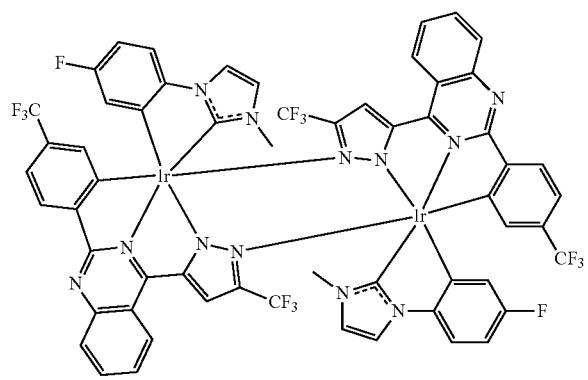
IA-24
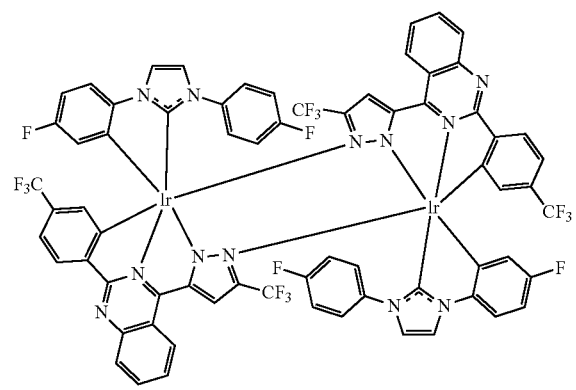
IA-25
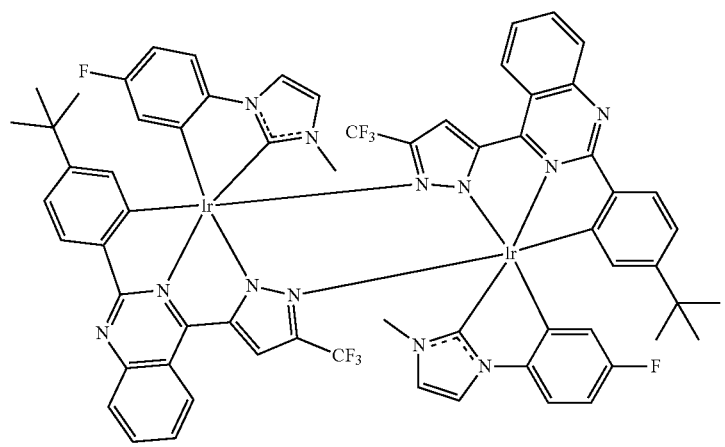
IA-26
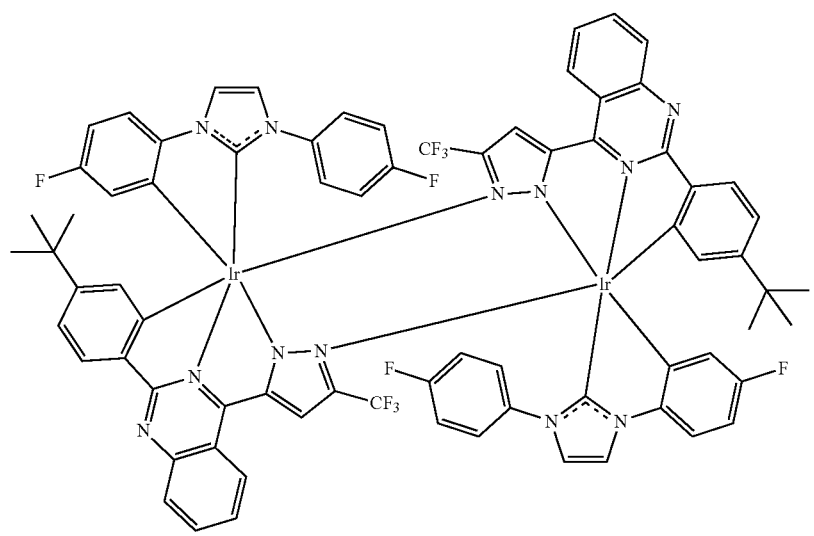

-continued
IA-27
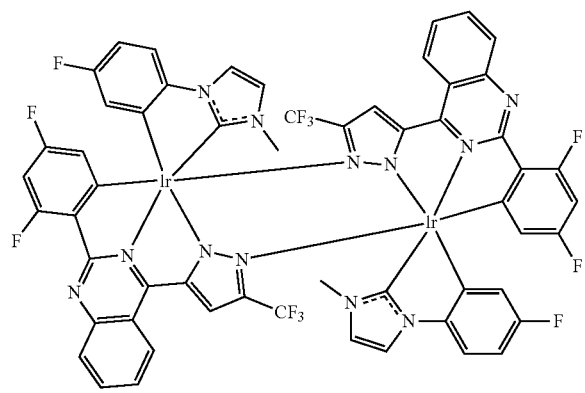
IA-28
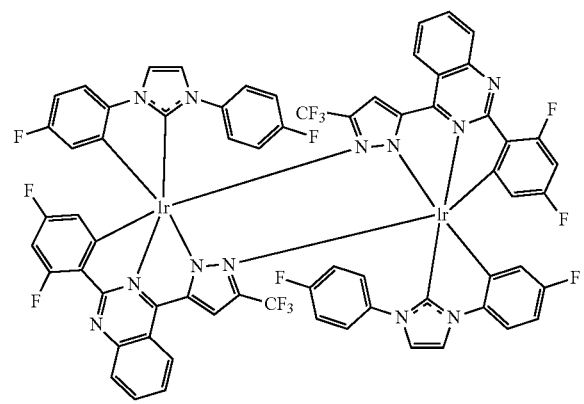
IA-29
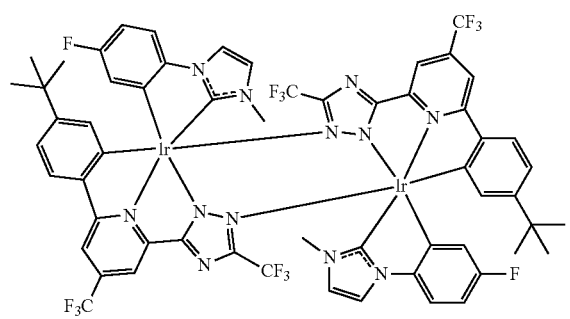
IA-30
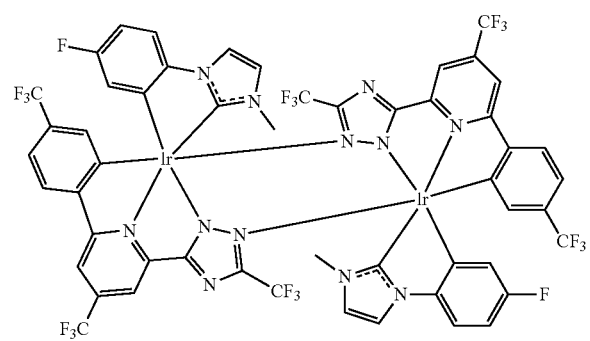
IA-31
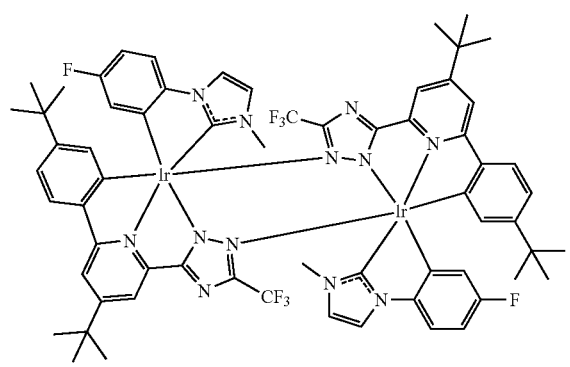
IA-32
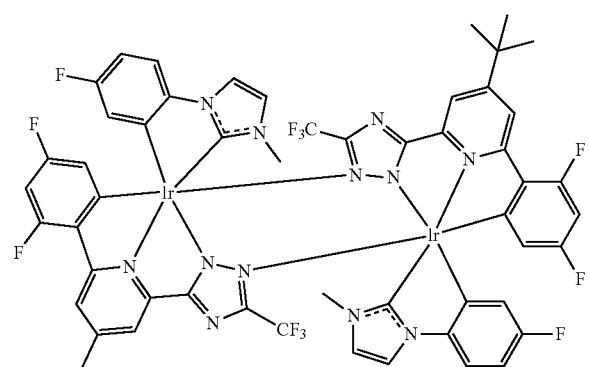
IA-33
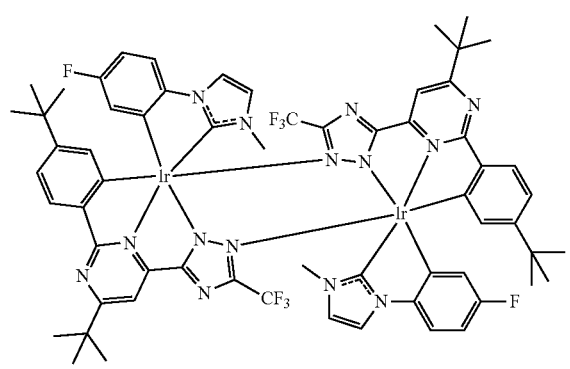
IA-34
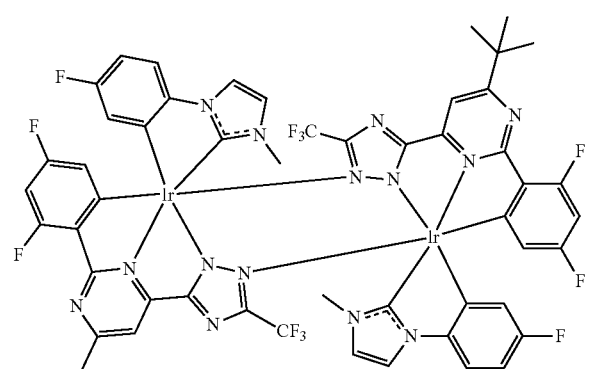

-continued
IA-35
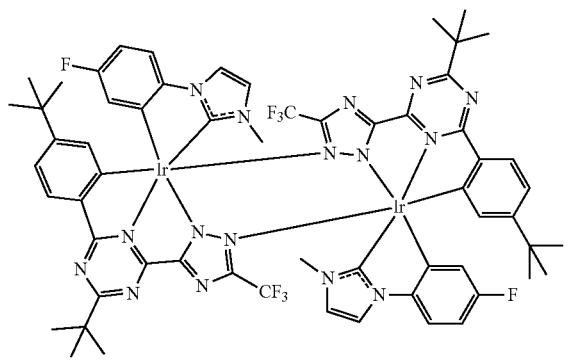
IA-36
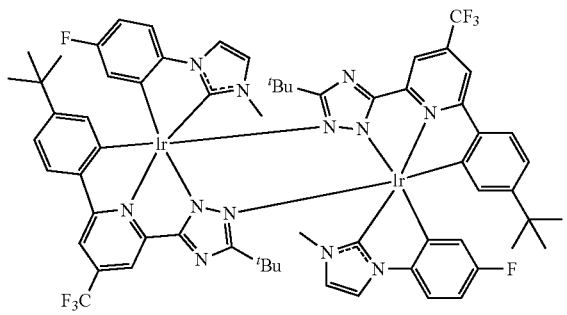
IA-37
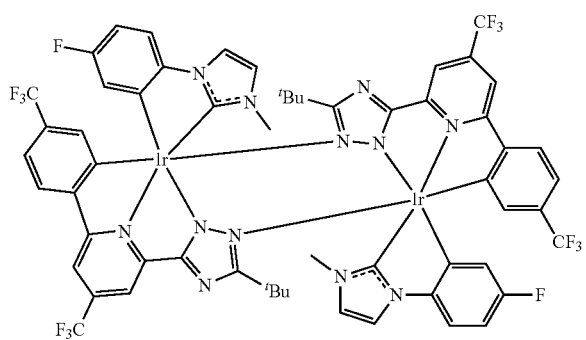
IA-38
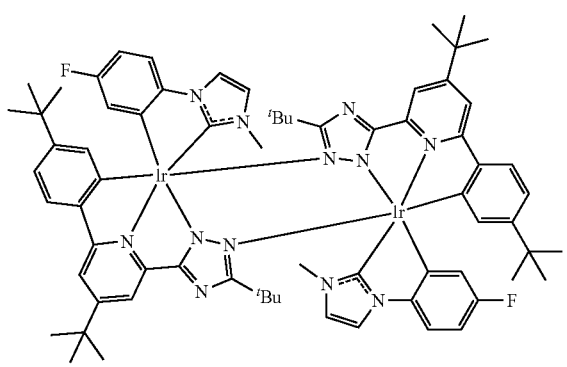
IA-39
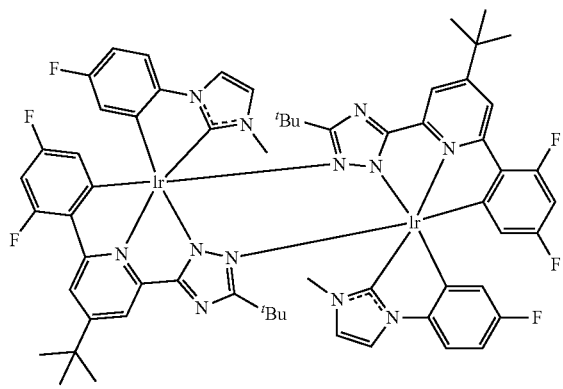
IA-40
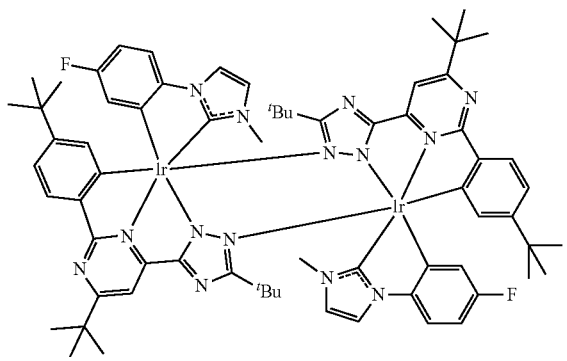
IA-41
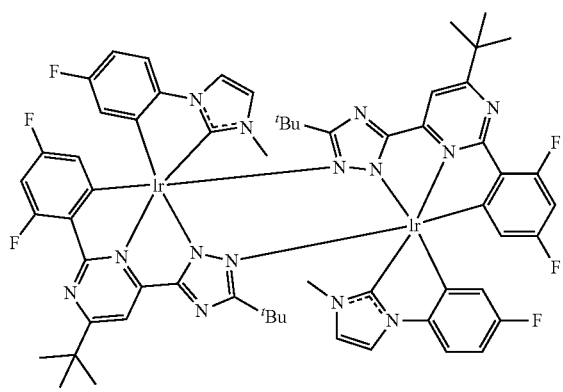
IA-42
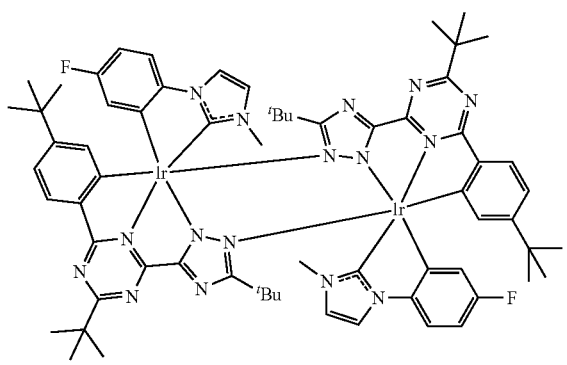

-continued

IA-43
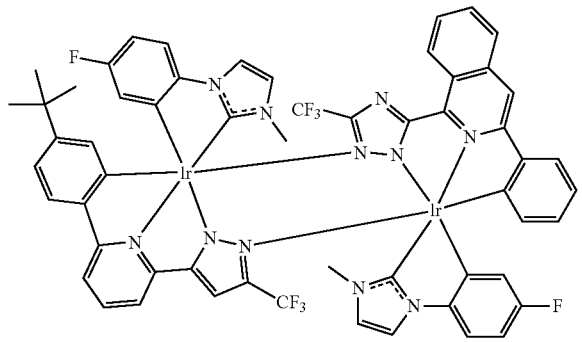

IA-44
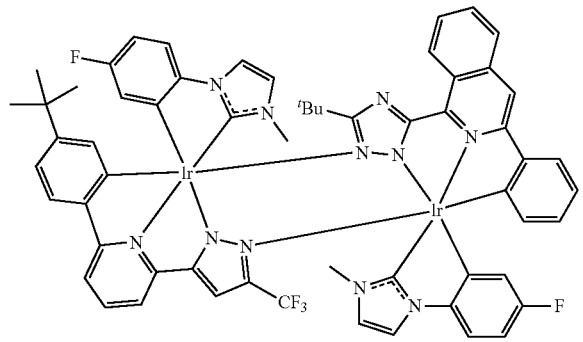

IA-45
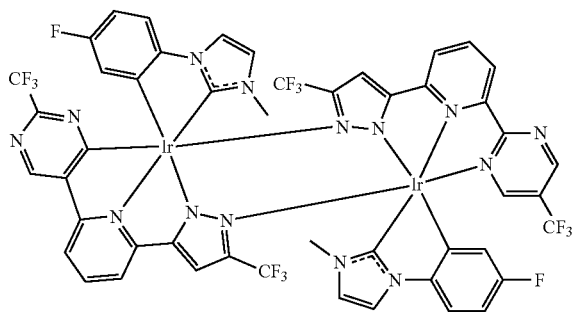

IA-46
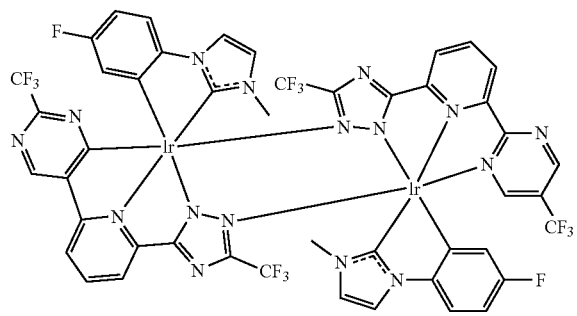

IA-47
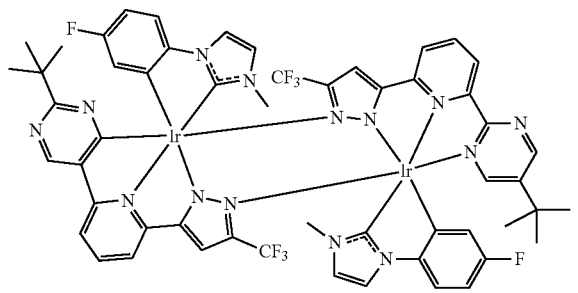

IA-48
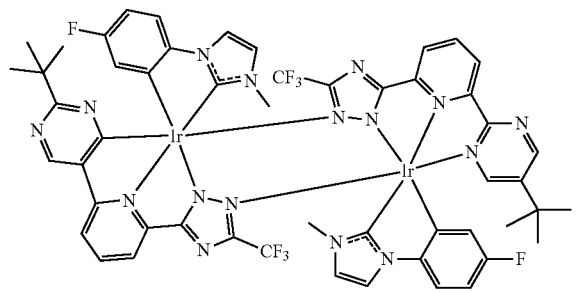

IA-49
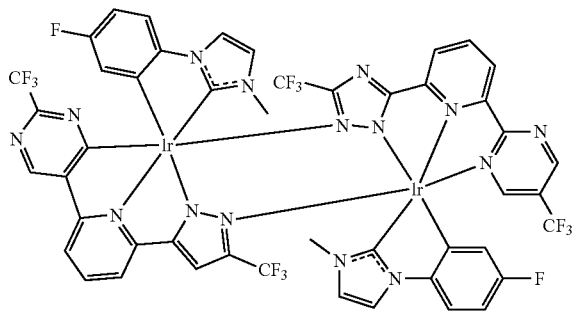

IA-50
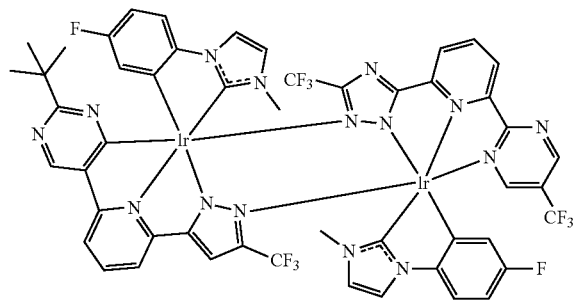

In an embodiment, the invention provides an OLED including two electrodes and a light-emitting layer disposed between the two electrodes, and the light-emitting layer contains the iridium complex. The iridium complex can be used as a dopant for a host material of the light-emitting layer. The material of each of the two electrodes can be selected from materials commonly used in the field, and other functional layers (such as an electron-transport layer, a hole-injection layer, a hole-transport layer, a hole-blocking layer or the like) can also be disposed between each of the electrodes and the light-emitting layer via a known technique in the art. The OLED can be manufactured on a flat substrate, such as conductive glass or a plastic substrate.

Besides, the iridium complex of the invention is easily synthesized and is convenient to purify, and is therefore suitable for commercial production.

In an embodiment, the iridium complex of the invention can be obtained by the following reaction, for example:

A specific example of the forming method of the iridium complex of the invention contains the following steps. First, a precursor of the first chelating ligand including A1, A2 and A3, a precursor of the second chelating ligand including A4 and A5, an iridium source, and other required reagents are mixed and heated to react. Then, the reaction mixture is purified by an appropriate method to obtain the iridium complex of the invention. The precursor of the first chelating ligand can be a tridentate chelating ligand, and the precursor of the second chelating ligand can be a bidentate carbene ligand, for example.

The iridium complex of the invention can be prepared by adopting suitable reactants and reaction conditions according to changes of each ligand, and the preparation method can be modified based on a known technique in the art.

In an embodiment, the iridium complex of the invention can also be obtained by the following reaction, for example:

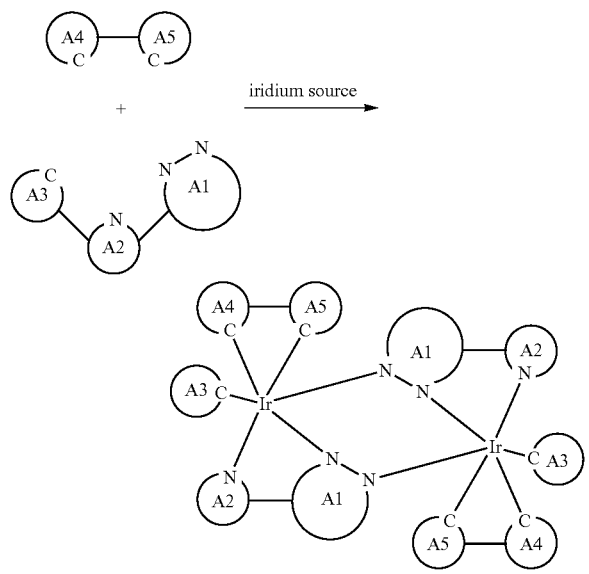
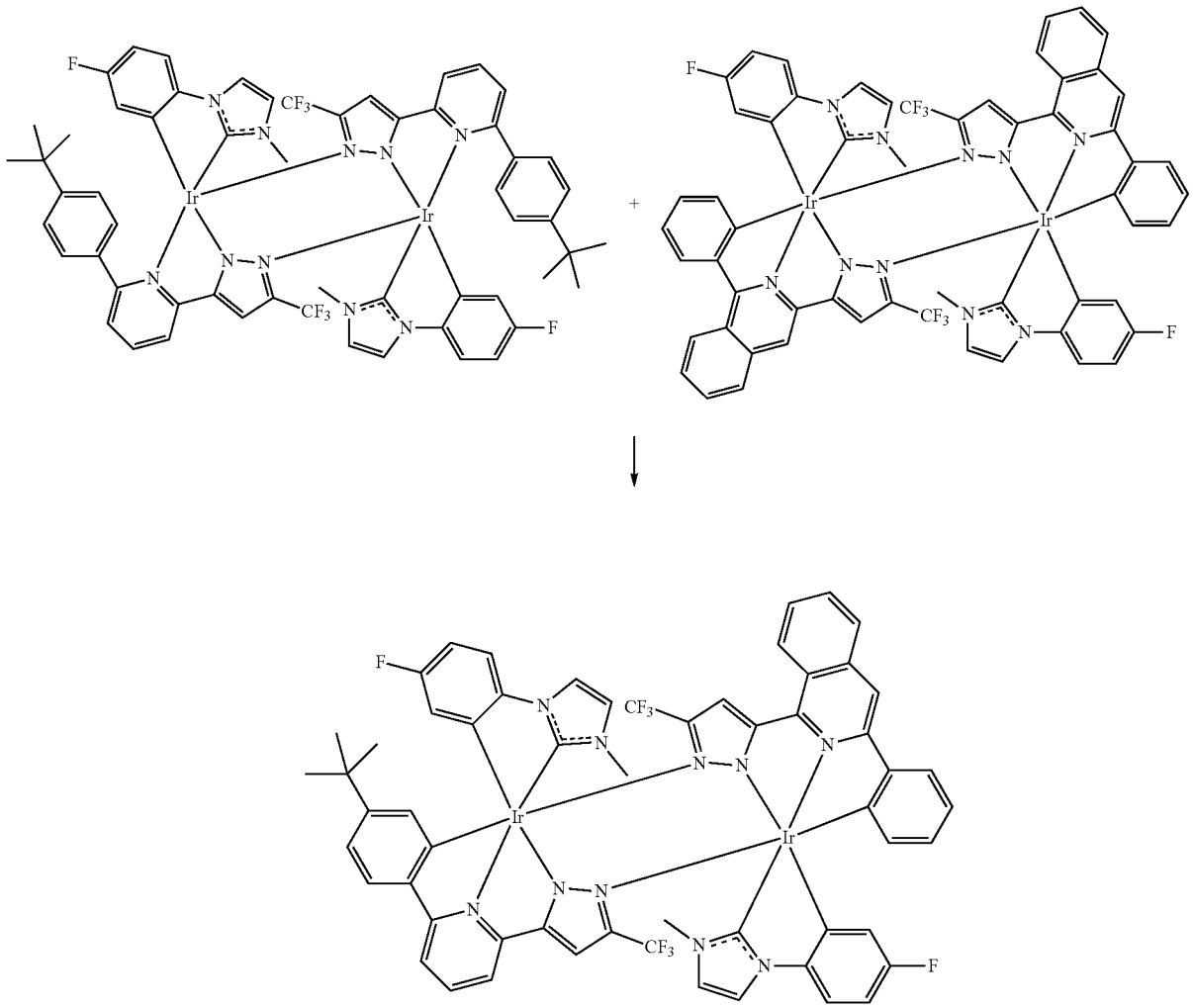

A specific example of the forming method of the iridium complex of the invention contains the following steps. First, a first iridium complex, a second iridium complex, and other required reagents are mixed and heated to react. Then, the reaction mixture is purified by appropriate method to obtain the iridium complex of the invention. The first iridium complex and the second iridium complex are structurally different, for example.

The iridium complex of the invention can be prepared by adopting suitable reactants and reaction conditions according to changes of each ligand, and the preparation method can be modified based on a known technique in the art.

In the following, several examples are provided to further describe the invention, but the examples are only exemplary and are not intended to limit the scope of the invention. The iridium complexes represented by formulas (IA-1), (IA-2), (IA-3), (IA-4), (IA-5) . . . are abbreviated as compounds (IA-1), (IA-2), (IA-3), (IA-4), (IA-5) . . . hereinafter. The abbreviations also apply to iridium complexes represented by other chemical structures in the following.

In the invention, the precursors of the chelating ligands having the structures illustrated in the following diagram are used in the synthesis of the iridium complex, for example.

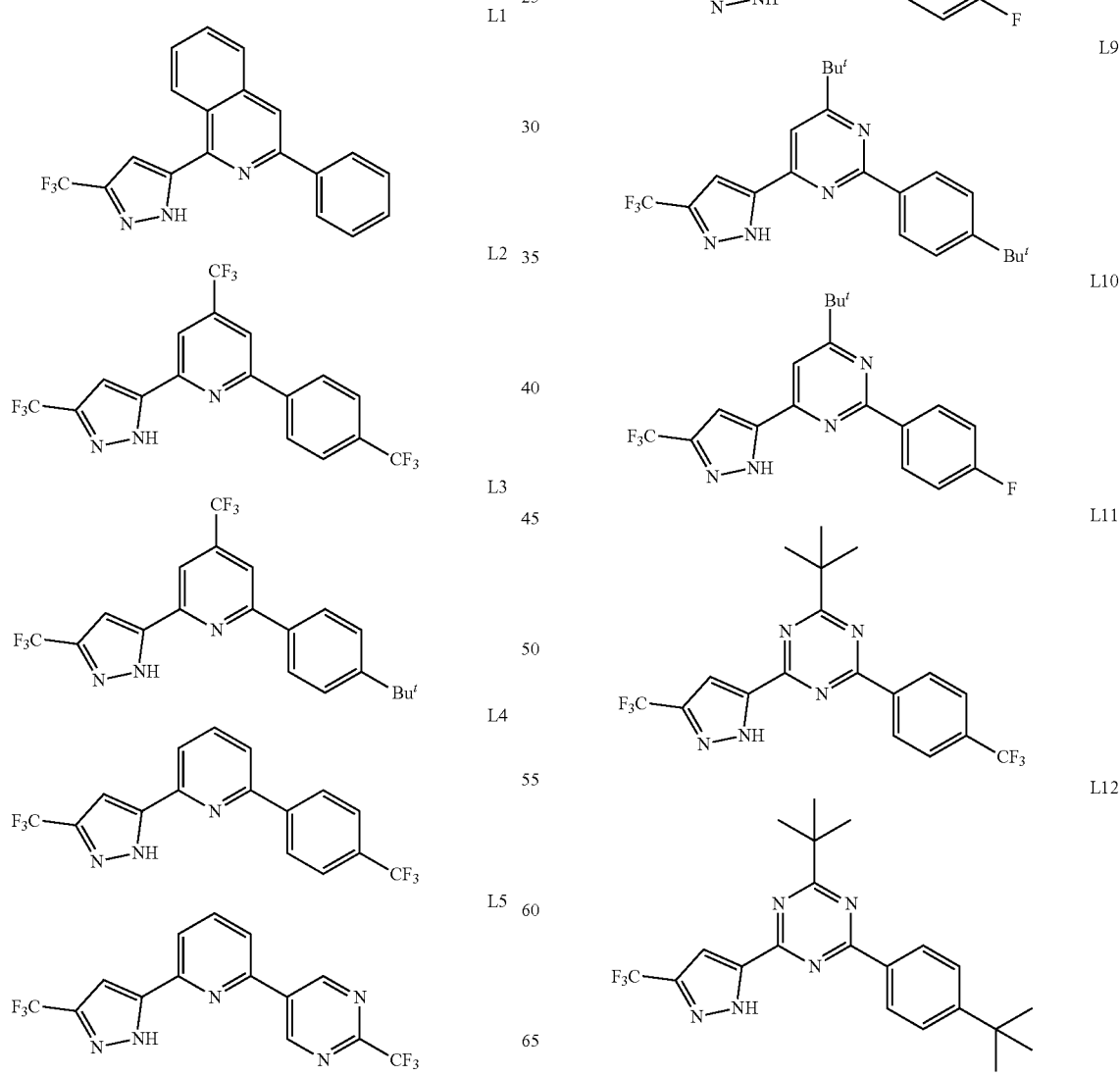

-continued

L13

L14

L15

L16

L17

L18

-continued

L19

L20

L21

L22

LC1

LC2

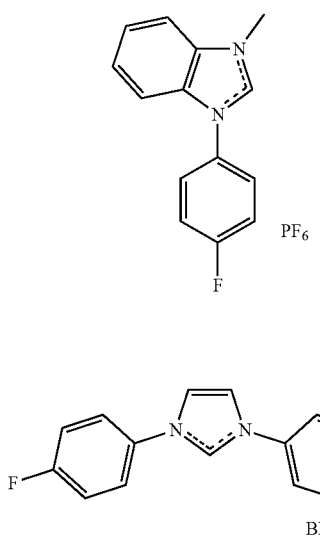

Example 1: Preparation of Compound (IA-1)

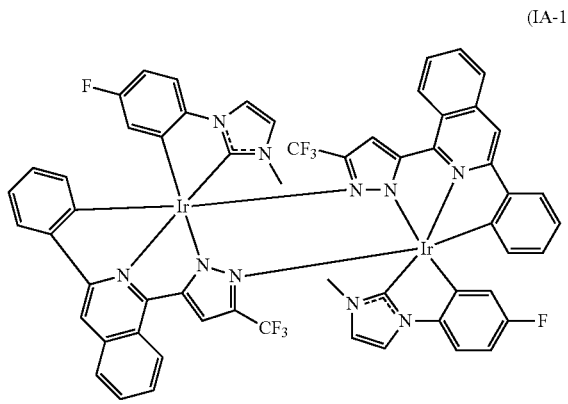

(IA-1)

IrCl$_3$·3H$_2$O (100 mg, 0.28 mmol, 1 eq), L1 (97 mg, 0.28 mmol, 1 eq), LC1 (92 mg, 0.28 mmol, 1 eq) and NaOAc (470 mg, 5.66 mmol, 20 eq) was taken in a Schlenk flask under N$_2$. The degassed propanoic acid (10 mL) was added to the mixture and the resulting solution was refluxed for 18 hrs. The mixture was cooled to RT. The solvent was removed under vacuum and the resulting residue was purified by column chromatography using ethyl acetate and hexane. Yield: 47.5% (95 mg, 0.13 mmol).

Spectral Data of Compound (IA-1):

$^1$H NMR (acetone-d$_6$, 400 MHz): δ 8.85 (d, J=8.44 Hz, 1H), 8.45 (s, 1H), 8.21 (d, J=8.12 Hz, 1H), 7.83 (m, 3H), 7.65 (s, 1H), 7.53 (s, 1H), 7.20 (m, 1H), 6.85 (s, 1H), 6.79 (t, 1H), 6.59 (t, 1H). 6.54 (dt, 1H), 5.60 (d, J=7.76 Hz, 1H), 5.23 (m, 1H), 2.57 (s, 3H).

$^{19}$F NMR (acetone-d$_6$, 376 MHz): δ −60.08 (s, 3F, Pz-CF$_3$), −120.10 (s, 1F, carbene-F). MS(FAB): m/z 1408.2, [M$^+$].

Example 2: Preparation of Compound (IA-2)

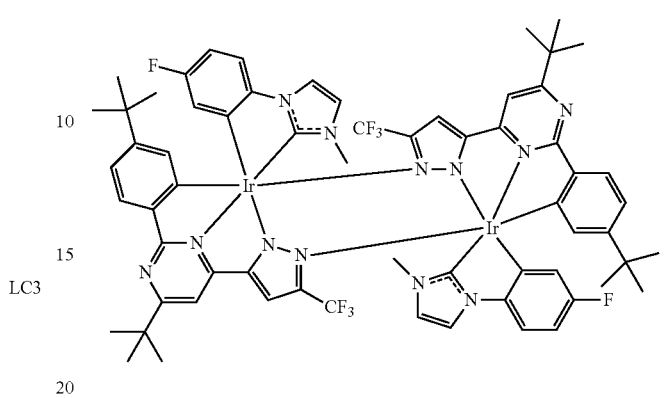

(IA-2)

[Ir(COD)Cl]$_2$ (84 mg, 0.12 mmol, 0.5 eq), L9 (100 mg, 0.24 mmol, 1 eq), LC1 (80 mg, 0.24 mmol, 1 eq) and sodium acetate (407 mg, 4.97 mmol, 20 eq) was taken in a Schlenk flask under N$_2$. The degassed decalin (10 mL) was added to the mixture and the resulting solution was refluxed for 12 hrs. The mixture was cooled to RT. The solvent was removed under vacuum and the resulting residue was purified by column chromatography using ethyl acetate and hexane. Yield: 48% (92 mg, 0.12 mmol).

Spectral Data of Compound (IA-2):

$^1$H NMR (acetone-d$_6$, 400 MHz): δ 7.95 (d, J=0.68 Hz, 1H), 7.84 (d, J=8.16 Hz, 1H), 7.68 (d, J=1.2 Hz, 1H), 7.29 (s, 1H), 7.22 (m, 1H), 6.93 (d, J=1.2 Hz, 1H), 6.86 (dd, J=8.16 Hz, 1H), 6.58 (m, 1H), 5.77 (s, 1H), 5.52 (m, 1H), 2.51 (s, 3H), 1.52 (s, 9H), 1.01 (s, 9H).

$^{19}$F NMR (acetone-d$_6$, 376 MHz): δ −60.63 (s, 3F, Pz-CF$_3$), −119.92 (s, 1F, carbene-F). MS(FAB): m/z 1536.4, [M$^−$].

Example 3: Preparation of Compound (IA-3)

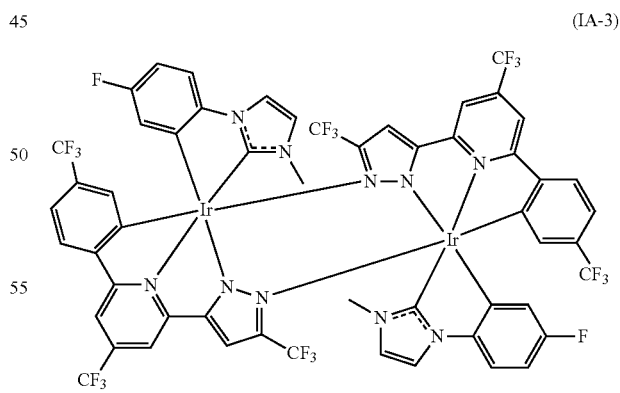

(IA-3)

[Ir(COD)Cl]$_2$ (40 mg, 0.05 mmol, 0.5 eq), L2 (50 mg, 0.11 mmol, 1 eq), LC1 (38 mg, 0.11 mmol, 1 eq) and sodium acetate (96 mg, 1.17 mmol, 10 eq) was taken in a Schlenk flask under N$_2$. The degassed decalin (10 mL) was added to the mixture and the resulting solution was refluxed for 10 hrs. The mixture was cooled to RT. The solvent was removed under vacuum and the resulting residue was purified by column chromatography using ethyl acetate and hexane. Yield: 23% (21 mg, 0.01 mmol).

Spectral Data of Compound (IA-3):

$^1$H NMR (CDCl$_3$, 400 MHz): δ 7.87 (s, 1H), 7.71 (s, 1H), 7.62 (d, J=8.2 Hz, 1H), 7.24 (m, 1H), 7.07 (d, J=8.28 Hz, 1H), 6.89 (m, 1H), 6.83 (s, 1H), 6.60 (m, 2H), 5.72 (s, 1H), 5.40 (dd, J=9.48 Hz, 1H), 2.39 (s, 3H).

$^{19}$F NMR (CDCl$_3$, 376 MHz): δ −60.71 (s, 3F, Pz-CF$_3$), −63.36 (s, 3F, Ph-CF$_3$), −64.48 (s, 3F, Pz-CF$_3$), −117.20 (s, 1F, carbene-F). MS(FAB): m/z 1580.0, [M$^+$].

Example 4: Preparation of Compound (IA-4)

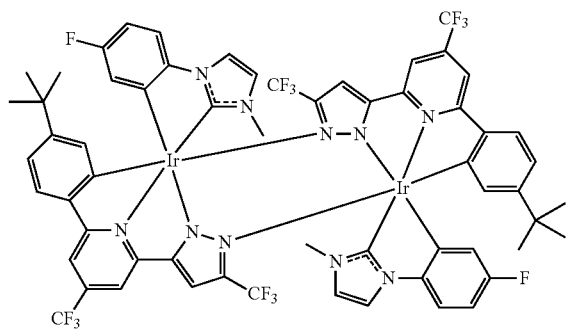

(IA-4)

[Ir(COD)Cl]$_2$ (82 mg, 0.12 mmol, 0.5 eq), L3 (100 mg, 0.24 mmol, 1 eq), LC1 (78 mg, 0.24 mmol, 1 eq) and sodium acetate (397 mg, 4.83 mmol, 20 eq) was taken in a Schlenk flask under N$_2$. The degassed decalin (10 mL) was added to the mixture and the resulting solution was refluxed for 14 hrs. The mixture was cooled to RT. The solvent was removed under vacuum and the resulting residue was purified by column chromatography using ethyl acetate and hexane. Yield: 47% (85 mg, 0.11 mmol).

Spectral Data of Compound (IA-4):

$^1$H NMR (acetone-d$_6$, 400 MHz): δ 8.18 (s, 2H), 7.75 (m, 2H), 7.29 (s, 1H), 7.26 (m, 1H), 6.98 (s, 1H), 6.87 (dd, J=8 Hz, 1H), 6.61 (dt, 1H), 5.79 (s, 1H), 5.5 (dd, J=10 Hz, 1H), 2.53 (s, 3H), 1.02 (s, 9H).

$^{19}$F NMR (acetone-d$_6$, 376 MHz): δ −60.63 (s, 3F, Pz-CF$_3$), −64.85 (s, 3F, Pyridine-CF$_3$), −119.87 (s, 1F, carbene-F). MS(FAB): m/z 1558.2, [M$^+$].

Example 5: Preparation of Compound (IA-5)

(IA-5)

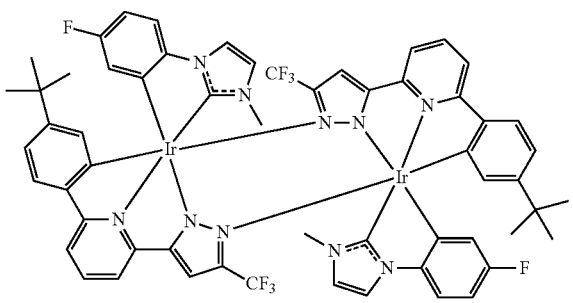

[Ir(COD)Cl]$_2$ (100 mg, 0.14 mmol, 0.5 eq), L6 (98 mg, 0.28 mmol, 1 eq), LC1 (92 mg, 0.28 mmol, 1 eq) and NaOAc (240 mg, 2.83 mmol, 10 eq) was taken in a Schlenk flask under N$_2$. The degassed decalin (10 mL) was added to the mixture and the resulting solution was refluxed for 24 hrs. The mixture was cooled to RT. The solvent was removed under vacuum and the resulting residue was purified by column chromatography using ethyl acetate and hexane. Yield: 53.6% (108 mg, 0.15 mmol).

Spectral Data of Compound (IA-5):

$^1$H NMR (acetone-d$_6$, 400 MHz): δ −7.92 (m, 3H), 7.65 (d, J=2.12 Hz, 1H), 7.52 (d, J=4.1 Hz, 1H), 7.20 (m, 1H), 7.00 (s, 1H), 6.91 (d, J=2.12 Hz, 1H), 6.79 (dd, J=8.2 Hz, 1H), 6.56 (dt, 1H), 5.75 (d, J=1.92 Hz, 1H), 5.52 (dd, J=10.8 Hz, 1H), 2.52 (s, 3H), 1.00 (s, 9H).

$^{19}$F NMR (acetone-d$_6$, 376 MHz): δ −60.36 (s, 3F, Pz-CF$_3$), −120.33 (s, 1F, carbene-F). MS(FAB): ink 1420.3, [M$^+$].

Example 6: Preparation of Compound (IA-6)

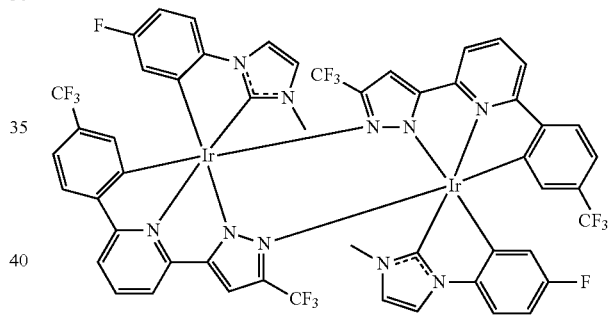

(IA-6)

[Ir(COD)Cl]$_2$ (100 mg, 0.14 mmol, 0.5 eq), L4 (92 mg, 0.28 mmol, 1 eq), LC1 (92 mg, 0.28 mmol, 1 eq) and NaOAc (240 mg, 2.83 mmol, 10 eq) was taken in a Schlenk flask under N$_2$. The degassed decalin (10 mL) was added to the mixture and the resulting solution was refluxed for 7 hrs. The mixture was cooled to RT. The solvent was removed under vacuum and the resulting residue was purified by column chromatography using ethyl acetate and hexane. Yield: 36.6% (75 mg, 0.10 mmol).

Spectral Data of Compound (IA-6):

$^1$H NMR (acetone-d$_6$, 400 MHz): δ 8.09 (m, 3H), 7.82 (d, J=8.12 Hz, 1H), 7.72 (d, J=2.08 Hz, 1H), 7.27 (m, 1H), 7.11 (s, 1H), 7.05 (d, J=8.04 Hz, 1H), 6.96 (d, J=2.04 Hz, 1H), 6.61 (m, 1H), 5.89 (s, 1H), 5.45 (dd, J=9.84 Hz, 1H), 2.50 (s, 3H).

$^{19}$F NMR (acetone-d$_6$, 376 MHz): δ −60.55 (s, 3F, Pz-CF$_3$), −63.45 (s, 3F, phenyl-CF$_3$), −119.59 (s, 1F, carbene-F). MS(FAB): m/z 1446.3, [M$^+$].

Example 7: Preparation of Compound (IA-7)

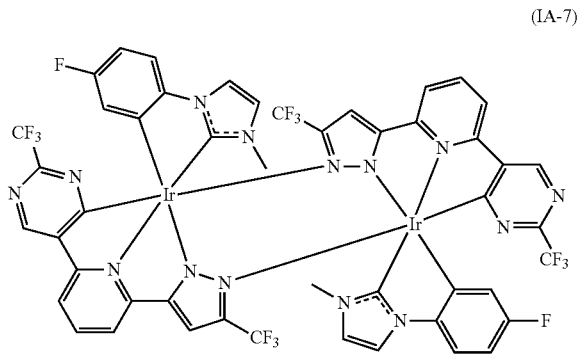

(IA-7)

IrCl$_3$·3H$_2$) (49 mg, 0.13 mmol, 1 eq), L5 (50 mg, 0.13 mmol, 1 eq), LC1 (45 mg, 0.13 mmol, 1 eq) and NaOAc (240 mg, 2.83 mmol, 20 eq) was taken in a Schlenk flask under N$_2$. The degassed propanoic acid (7 mL) was added to the mixture and the resulting solution was refluxed for 20 hrs. The mixture was cooled to RT. The solvent was removed under vacuum and the resulting residue was purified by column chromatography using ethyl acetate and hexane. Yield: 12% (12 mg, 0.01 mmol).

Spectral Data of Compound (IA-7):

$^1$H NMR (acetone-d$_6$, 400 MHz): δ 8.71 (s, 1H), 8.29 (m, 1H), 8.20 (m, 2H), 7.55 (d, J=2.08 Hz, 1H), 7.24 (m, 2H), 6.83 (d, J=2.08 Hz, 1H), 6.68 (m, 1H), 5.46 (dd, J=9.68 Hz, 1H), 2.51 (s, 3H).
$^{19}$F NMR (acetone-d$_6$, 376 MHz): δ −60.88 (s, 3F, Pz-CF$_3$), −71.48 (s, 3F, pyrimidine-CF$_3$), −119.77 (s, 1F, carbene-F). MS(FAB): m/z 1448.2, [M$^+$].

Example 8: Preparation of Compound (IA-8)

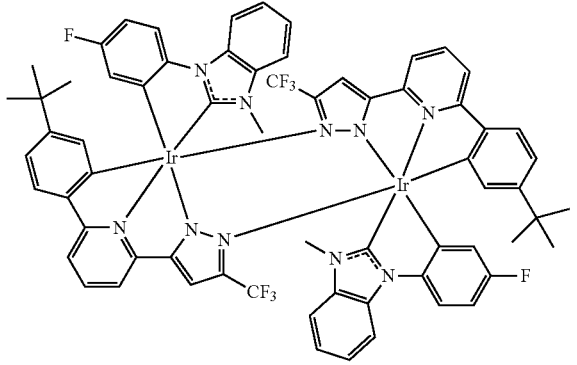

(IA-8)

Ir(COD)Cl]$_2$ (100 mg, 0.14 mmol, 0.5 eq), L6 (100 mg, 0.28 mmol, 1 eq), LC2 (108 mg, 0.29 mmol, 1 eq) and NaOAc (500 mg, 6.09 mmol, 20 eq) was taken in a Schlenk flask under N$_2$. The degassed decalin (10 mL) was added to the mixture and the resulting solution was refluxed for 24 hrs. The mixture was cooled to RT. The solvent was removed under vacuum and the resulting residue was purified by column chromatography using ethyl acetate and hexane. Yield: 47% (107 mg, 0.14 mmol).

Spectral Data of Compound (IA-8):

$^1$H NMR (acetone-d$_6$, 400 MHz): δ 7.98 (m, 1H), 7.89 (m, 2H), 7.50 (d, J=7.96 Hz, 1H), 7.36 (m, 2H), 7.07 (m, 4H), 6.72 (m, 2H), 5.62 (dd, J=10 Hz, 1H), 5.44 (s, 1H), 2.75 (s, 3H), 0.63 (s, 9H).
$^{19}$F NMR (acetone-d$_6$, 376 MHz): δ −60.28 (s, 3F, Pz-CF$_3$), −119.66 (s, 1F, carbene-F). MS(FAB): m/z 1522.4, [M$^+$].

Example 9: Preparation of Compound (IA-9)

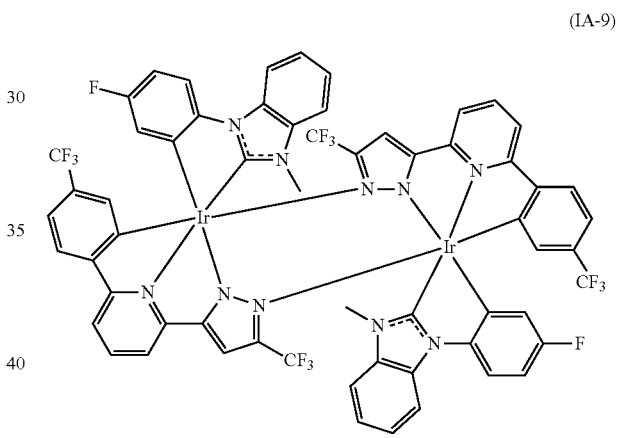

(IA-9)

Ir(COD)Cl]$_2$ (100 mg, 0.15 mmol, 0.5 eq), L4 (92 mg, 0.29 mmol, 1 eq), LC2 (108 mg, 0.29 mmol, 1 eq) and NaOAc (500 mg, 6.09 mmol, 20 eq) was taken in a Schlenk flask under N$_2$. The degassed decalin (10 mL) was added to the mixture and the resulting solution was refluxed for 24 hrs. The mixture was cooled to RT. The solvent was removed under vacuum and the resulting residue was purified by column chromatography using ethyl acetate and hexane. Yield: 44% (102 mg, 0.13 mmol).

Spectral Data of Compound (IA-9):

$^1$H NMR (acetone-d$_6$, 400 MHz): δ −8.14 (m, 3H), 7.83 (d, J=8.16 Hz, 1H), 7.41 (m, 2H), 7.19 (s, 1H), 7.18 (m, 2H), 7.04 (m, 2H), 6.73 (m, 1H), 5.62 (d, J=6.7 Hz, 1H), 5.54 (dd, J=9.8 Hz, 1H), 2.75 (s, 3H).
$^{19}$F NMR (acetone-d$_6$, 376 MHz): δ −60.42 (s, 3F, Pz-CF$_3$), 63.94 (s, 3F, phenyl-CF$_3$), −118.93 (s, 1F, carbene-F). MS(FAB): m/z 1546.2, [M$^+$].

Example 10: Preparation of Compound (IA-10)

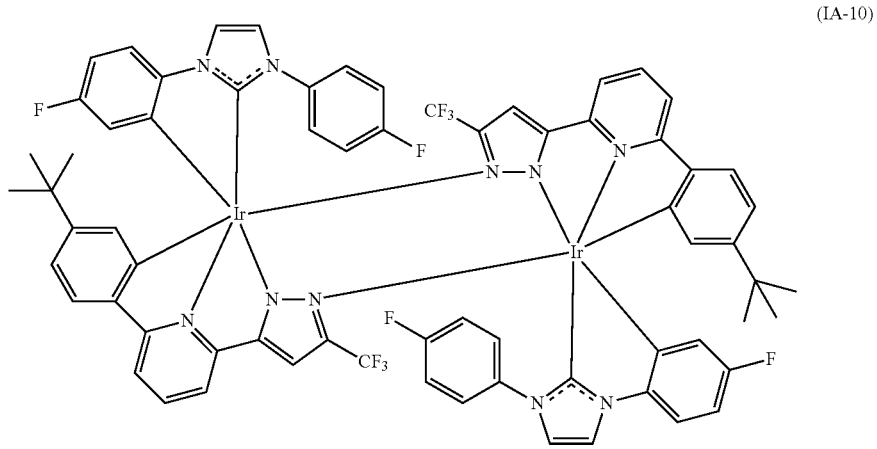

(IA-10)

Ir(COD)Cl]₂ (100 mg, 0.15 mmol, 0.5 eq), L6 (107 mg, 0.30 mmol, 1 eq), LC3 (103 mg, 0.30 mmol, 1 eq) and NaOAc (250 mg, 2.97 mmol, 10 eq) was taken in a Schlenk flask under N₂. The degassed decalin (10 mL) was added to the mixture and the resulting solution was refluxed for 12 hrs. The mixture was cooled to RT. The solvent was removed under vacuum and the resulting residue was purified by column chromatography using ethyl acetate and hexane. Yield: 38% (91 mg, 0.11 mmol).

Spectral Data of Compound (IA-10):

$^1$H NMR (CDCl₃, 400 MHz): δ 7.67 (t, H), 7.59 (dd, J=8.12 Hz, 1H), 7.21 (dd, J=7.6 Hz, 1H), 7.03 (m, 1H), 6.81 (m, 2H), 6.67 (dt, 1H), 6.32 (m, 4H), 5.65 (d, J=1.84 Hz, 1H), 5.26 (dd, J=10.04 Hz, 1H), 0.87 (s, 9H).

$^{19}$F NMR (CDCl₃, 376 MHz): δ −60.39 (s, 3F, Pz-CF₃), −116.07 (s, 1F, carbene-F), −118.24 (s, 1F, carbene-F). MS(FAB): m/z 1582.5, [M⁺].

Example 11: Preparation of Compound (IA-11)

[Ir(COD)Cl]₂ (100 mg, 0.15 mmol, 0.5 eq), L4 (105 mg, 0.30 mmol, 1 eq), LC3 (103 mg, 0.30 mmol, 1 eq) and NaOAc (250 mg, 2.97 mmol, 10 eq) was taken in a Schlenk flask under N₂. The degassed decalin (10 mL) was added to the mixture and the resulting solution was refluxed for 12 hrs. The mixture was cooled to RT. The solvent was removed under vacuum and the resulting residue was purified by column chromatography using ethyl acetate and hexane. Yield: 35% (82 mg, 0.10 mmol)

Spectral Data of Compound (IA-11):

$^1$H NMR (CDCl₃, 400 MHz): δ 7.78 (m, 2H), 7.58 (d, J=8.12 Hz, 1H), 7.52 (d, J=2.12 Hz, 1H), 7.35 (d, J=7.56 Hz, 1H), 7.08 (m, 2H), 6.84 (m, 1H), 6.72 (dt, 1H), 6.34 (m, 3H), 6.17 (br, 1H), 5.76 (s, 1H), 5.19 (dd, J=9.82 Hz, 1H).

$^{19}$F NMR (CDCl₃, 376 MHz): δ −60.46 (s, 3F, Pz-CF₃), −63.16 (s, 3F, Ph-CF₃), −115.42 (s, 1F, carbene-F), −117.63 (s, 1F, carbene-F). MS(FAB): mz 1604.2, [M⁺].

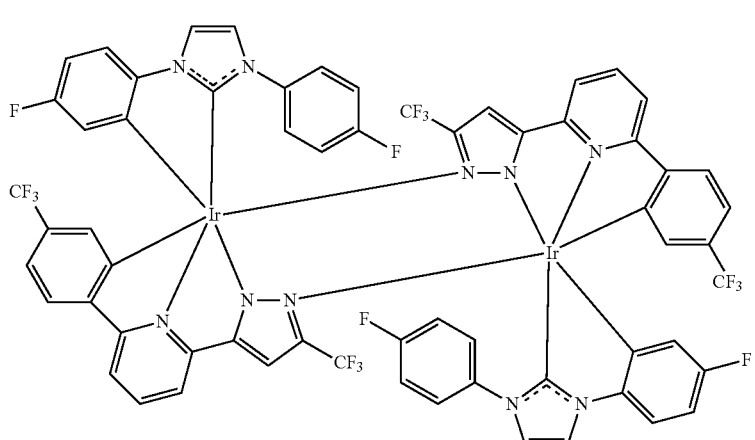

(IA-11)

Example 12: Preparation of Compound (IA-12)

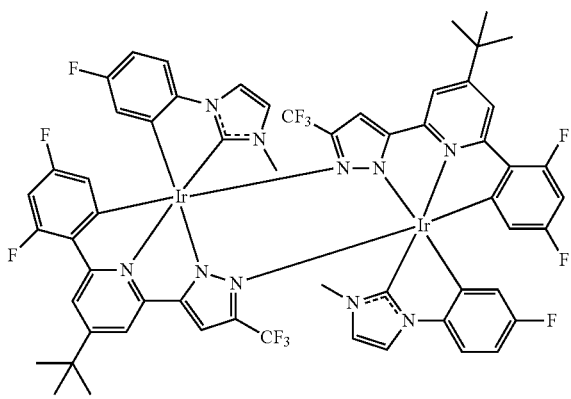
(IA-12)

IrCl$_3$·3H$_2$O (100 mg, 0.28 mmol, 1 eq), L7 (110 mg, 0.28 mmol, 1 eq), LC1 (90 mg, 0.28 mmol, 1 eq) and NaOAc (480 mg, 5.66 mmol, 20 eq) was taken in a Schlenk flask under N$_2$. The degassed propanoic acid (10 mL) was, added to the mixture and the resulting solution was refluxed for 24 hrs. The mixture was cooled to RT. The solvent was removed under vacuum and the resulting residue was purified by column chromatography using ethyl acetate and hexane. Yield: 32% (68 mg, 0.09 mmol).

Spectral Data of Compound (IA-12):
$^1$H NMR (acetone-d$_6$, 400 MHz): δ 8.12 (m, 2H), 7.70 (d, J=2.12 Hz, 1H), 7.28 (m, 1H), 7.22 (s, 1H), 6.93 (d, J=1.04 Hz, 1H), 6.64 (dt, 1H), 6.41 (m, 1H), 5.41 (dd, J=9.9 Hz, 1H), 5.04 (dd, J=9.88 Hz, 1H), 2.49 (s, 3H), 1.51 (s, 9H).
$^{19}$F NMR (acetone-d$_6$, 376 MHz): δ −60.51 (s, 3F, Pz-CF$_3$), −110.35 (d, 1F, Ph-F), −112.73 (d, 1F, Ph-F), −119.34 (s, 1F, carbene-F). MS(FAB): m/z 1494.2, [M$^+$].

Example 13: Preparation of Compound (IA-13)

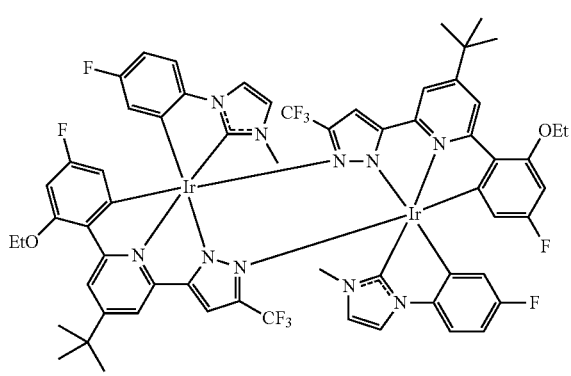
(IA-13)

[Ir(COD)Cl]$_2$ (84 mg, 0.12 mmol, 0.5 eq), L8 (102 mg, 0.24 mmol, 1 eq), LC1 (80 mg, 0.24 mmol, 1 eq) and NaOAc (407 mg, 4.97 mmol, 20 eq) was taken in a Schlenk flask under N$_2$. The degassed decalin (10 mL) was added to the mixture and the resulting solution was refluxed for 12 hrs. The mixture was cooled to RT. The solvent was removed under vacuum and the resulting residue was purified by column chromatography using ethyl acetate and hexane. Yield: 21% (41 mg, 0.05 mmol).

Spectral Data of Compound (IA-13):
$^1$H NMR (acetone-d$_6$, 400 MHz): δ 8.70 (d, J=1.8 Hz, 1H), 7.96 (d, J=1.8 Hz, 1H), 7.63 (d, J=2.08 Hz, 1H), 7.22 (m, 1H), 7.11 (s, 1H), 6.86 (d, J=2.08 Hz, 1H), 6.60 (m, 1H), 6.21 (dd, J=11.52 Hz, 1H), 5.42 (dd, J=10 Hz, 1H), 4.85 (dd, J=9.96 Hz, 1H), 4.16 (m, 2H), 2.47 (s, 3H), 1.59 (t, J=6.92 Hz, 3H), 1.5 (s, 9H).
$^{19}$F NMR (acetone-d$_6$, 376 MHz): δ −60.26 (s, 3F, Pz-CF$_3$), −111.42 (d, 1F, Ph-F), −119.77 (s, 1F, carbene-F). MS(FAB): m/z 1544.2, [M$^+$].

Example 14: Preparation of Compound (IA-14)

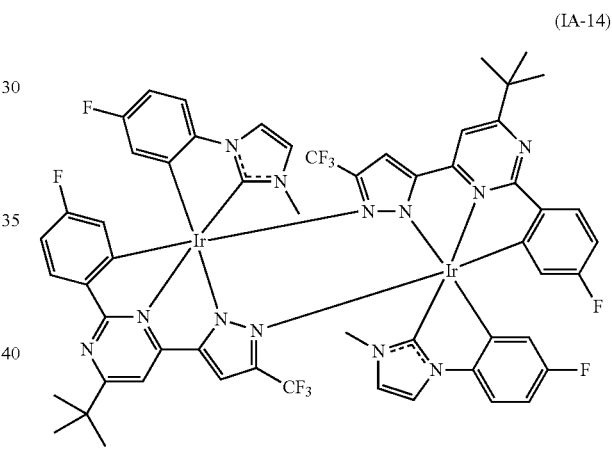
(IA-14)

[Ir(COD)Cl]$_2$ (84 mg, 0.12 mmol, 0.5 eq), L10 (90 mg, 0.24 mmol, 1 eq), LC1 (80 mg, 0.24 mmol, 1 eq) and sodium acetate (407 mg, 4.97 mmol, 20 eq) was taken in a Schlenk flask under N$_2$. The degassed decalin (10 mL) was added to the mixture and the resulting solution was refluxed for 12 hrs. The mixture was cooled to RT. The solvent was removed under vacuum and the resulting residue was purified by column chromatography using ethyl acetate and hexane. Yield: 37% (67 mg, 0.09 mmol).

Spectral Data of Compound (IA-14):
$^1$H NMR (acetone-d$_6$, 400 MHz): δ 8.03 (s, 1H), 8.00 (dd, J=6.4 Hz, 1H), 7.71 (d, J=0.2.08 Hz, 1H), 7.35 (s, 1H), 7.28 (dd, J=4.92 Hz, 1H), 6.94 (d, J=2.04 Hz, 1H), 6.63~6.55 (m, 2H), 5.47 (dd, J=9.76 Hz, 1H), 5.26 (dd, J=10.6 Hz, 1H), 2.50 (s, 3H), 1.53 (s, 9H).
$^{19}$F NMR (acetone-d$_6$, 376 MHz): δ −60.71 (s, 3F, Pz-CF$_3$), −109.65 (s, 1F, Ph-F) −119.37 (s, 1F, carbene-F). MS(FAB): m/z 1460.3, [M$^+$].

Example 15: Preparation of Compound (IA-15)

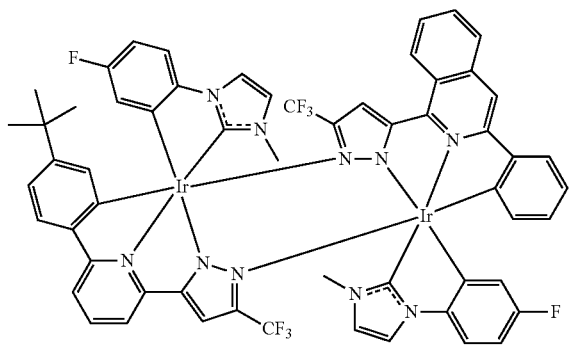

(IA-15)

Red emitting iridium complex (IA-1) (20 mg, 0.014 mmol, 1 eq) and the greenish blue emitting iridium complex (IA-5) (20 mg, 0.014 mmol, 1 eq) was taken in a Schlenk flask under $N_2$. The degassed DGME (10 mL) was added to the mixture and the resulting solution was refluxed for 2 days. The mixture was cooled to RT. The solvent was removed under vacuum and the residue was purified by column chromatography using ethyl acetate and hexane. Yield: 30% (12 mg, 0.0084 mmol).

Spectral Data of Compound (IA-15):

$^1$H NMR (acetone-$d_6$, 400 MHz): δ 8.86 (d, J=8.32 Hz, 1H), 8.42 (s, 1H), 8.20 (d, J=7.8 Hz, 1H), 7.94-7.86 (m, 2H), 7.83-7.75 (m, 3H), 7.72 (dd, J=7.8 Hz, 1H), 7.68 (d, J=2.12 Hz, 1H), 7.63 (d, J=2.12 Hz, 1H), 7.54 (s, 1H), 7.53 (d, J=8.24 Hz, 1H), 7.21-7.16 (m, 2H), 7.01 (s, 1H), 6.93 (d, J=2.08 Hz, 1H), 6.83 (d, J=2.08 Hz, 1H), 6.80-6.73 (m, 2H), 6.58-6.48 (m, 3H), 5.73 (d, J=1.88 Hz, 1H), 5.61 (dd, J=7.72 Hz, 1H), 5.51 (dd, J=10.08 Hz, 1H), 5.25 (dd, J=10.08 Hz, 1H), 2.56 (s, 3H), 2.52 (s, 3H), 1.01 (s, 9H).

$^{19}$F NMR (acetone-$d_6$, 376 MHz): δ -60.21 (s, 3F, Pz-$CF_3$), -60.24 (s, 3F, Pz-$CF_3$), -120.17 (s, 1F, carbene-F), -120.27 (s, 1F, carbene-F).

Figure 2:
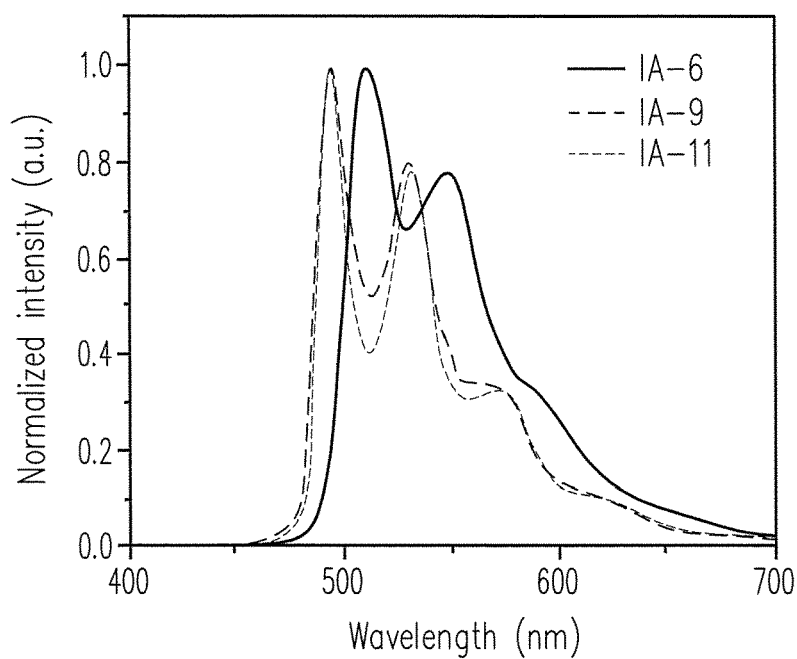
FIG. 2 shows the emission spectrum of each of compounds (IA-6), (IA-9) and (IA-11).
Figure 3:
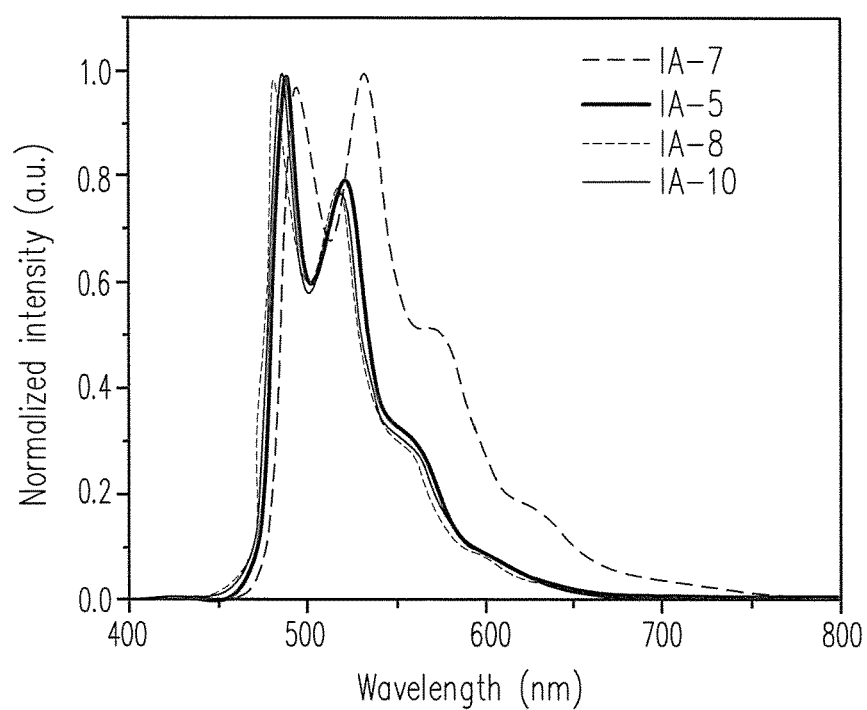
FIG. 3 shows the emission spectrum of each of compounds (IA-5), (IA-7), (IA-8) and (IA-10).
Figure 4:
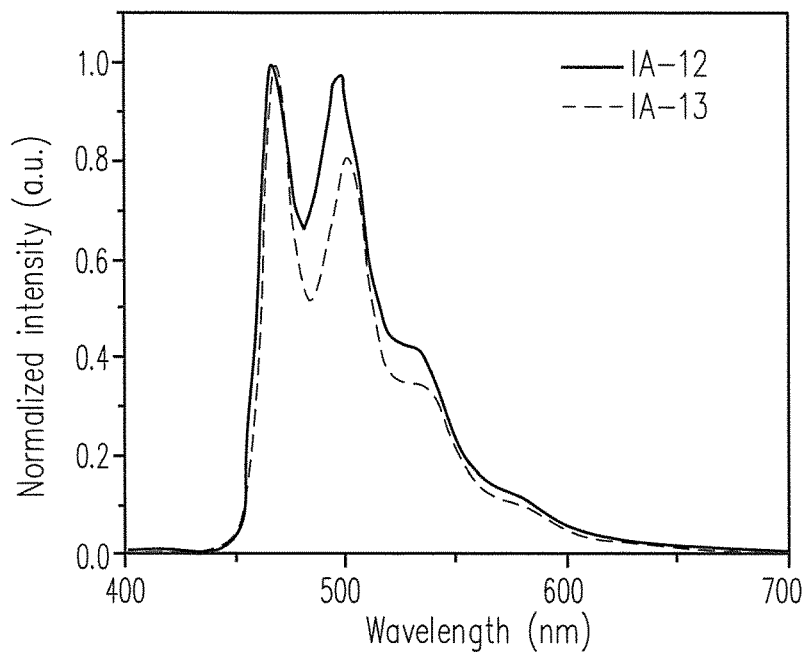
FIG. 4 shows the emission spectrum of each of compounds (IA-12) and (IA-13).
Figure 5:
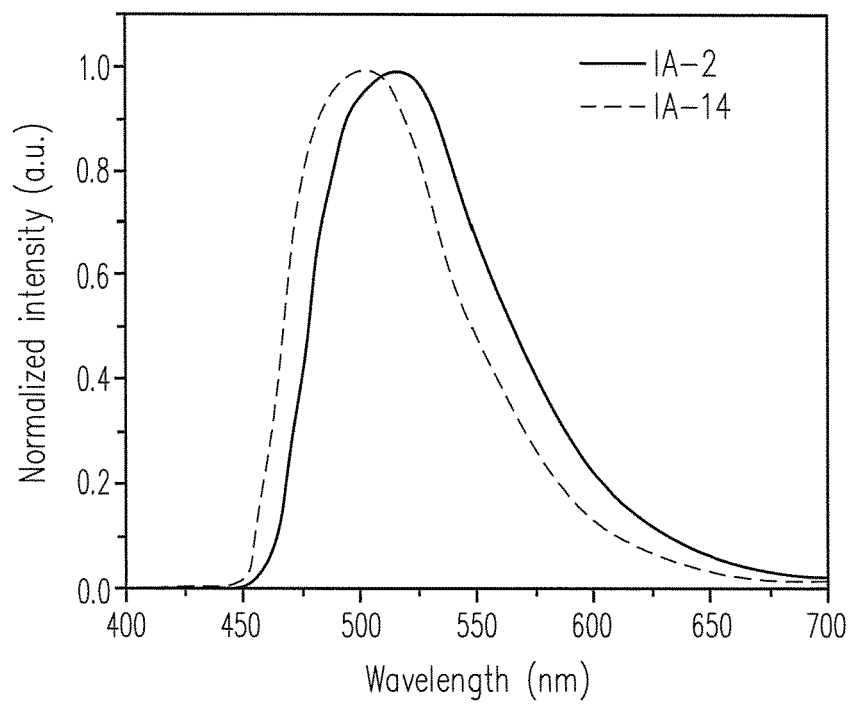
FIG. 5 shows the emission spectrum of each of compounds (IA-2) and (IA-14).
Figure 6:
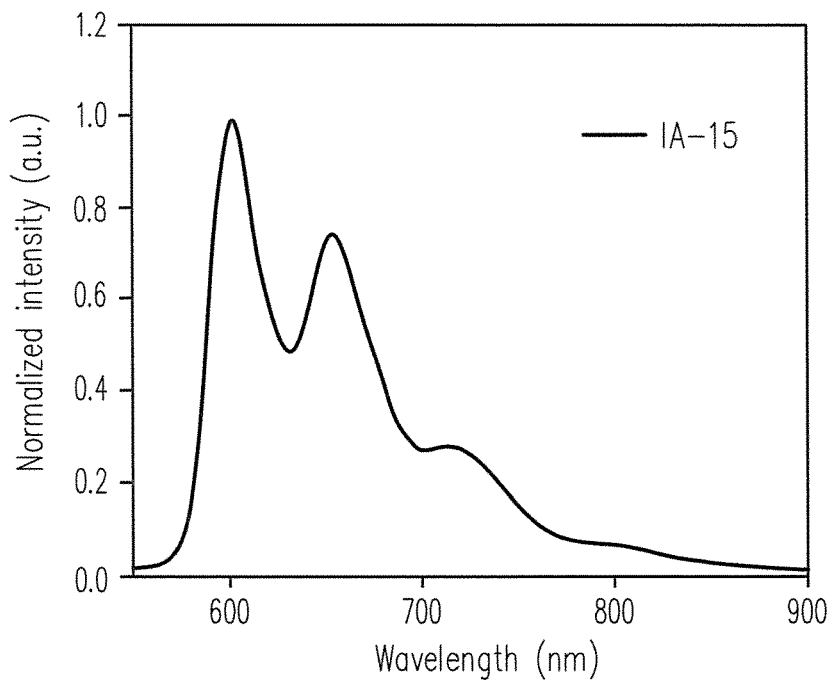
FIG. 6 shows the emission spectrum of compound (IA-15).

FIG. 1 shows the emission spectrum of each of compounds (IA-1) and (IA-4). FIG. 2 shows the emission spectrum of each of compounds (IA-6), (IA-9) and (IA-11). FIG. 3 shows the emission spectrum of each of compounds (IA-5), (IA-7), (IA-8) and (IA-10). FIG. 4 shows the emission spectrum of each of compounds (IA-12) and (IA-13). FIG. 5 shows the emission spectrum of each of compounds (IA-2) and (IA-14). FIG. 6 shows the emission spectrum of compound (IA-15). The absorption peak location (abs $\lambda_{max}$), emission peak location (em. $\lambda_{max}$), quantum yield (Φ), and emission lifetime ($\tau_{obs}$) of the above-mentioned compounds are shown in Table 1 below.

TABLE 1

| Compound | abs. $\lambda_{max}$ (nm)[a] | em. $\lambda_{max}$ (nm)[b] | Φ (%)[b] | $\tau_{obs}$ (μs)[b] |
|---|---|---|---|---|
| IA-1 | 292, 309, 352, 455 | 600, 653, 711 | 73.6 | 8.90 |
| IA-2 | 282, 262 | 516 | 52.2 | 1.36 |
| IA-4 | 288, 340, 385 | 531 | 98.8 | 3.00 |
| IA-5 | 281, 311, 368 | 487, 521, 559 | 95.8 | 4.58 |
| IA-6 | 276, 311, 348 | 511, 545, 594 | 81.3 | 2.80 |
| IA-7 | 290 | 494, 530, 571 | 44.1 | 2.38 |
| IA-8 | 304, 359, 435 | 483, 517, 553 | 91.5 | 4.46 |
| IA-9 | 306, 364, 438 | 494, 531, 570 | 58.2 | 4.29 |
| IA-10 | 324, 398 | 485, 519, 554 | 64.0 | 6.32 |
| IA-11 | 307, 409 | 494, 532, 570 | 65.4 | 4.91 |
| IA-12 | 275, 303 | 466, 496, 532 | 89.5 | 3.49 |
| IA-13 | 288, 330 | 468, 500, 536 | 100 | 4.78 |
| IA-14 | 302, 367 | 505 | 87.0 | 1.93 |
| IA-15 | 277, 309, 396 | 603, 654, 717 | 64.8 | 8.64 |

[a]Absorption spectra were measured in $CH_2Cl_2$ solution with a concentration of $10^{-5}$ M.
[b]Photo-luminescent (PL) spectra, quantum yields, and lifetime were measured in degassed $CH_2Cl_2$ solution.

It is clear from FIGS. 1-5 and Table 1 that the iridium complexes of the invention not only have high quantum yields and excellent luminous efficiencies, but also cover a wide range of emission wavelength. Therefore, the iridium complexes of the invention are very competitive in the industry.

In summary, the iridium complex of the invention has strong rigidity and high stability, and the luminous efficiency thereof is accordingly increased. Furthermore, the iridium complex of the invention can be synthesized from an iridium precursor, a chelating tridentate and a bidentate carbene ligand by a one-step process rather than complicated process steps. Moreover, the emission wavelength of the iridium complex can be easily adjusted by varying the substituent(s) on the tridentate ligand(s) and/or bidentate carbene ligand(s). Therefore, wide range of emission wavelength of the iridium complex can be achieved, so the application of the iridium complex of the invention is very broad.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An iridium complex represented by general formula (I):

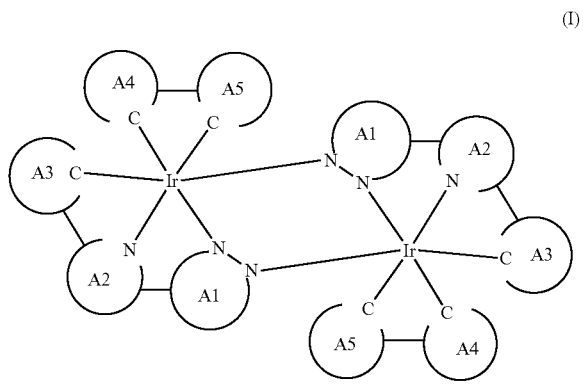

(I)

wherein

A1, A2, A3, A4 and A5 are each independently a 5-membered unsaturated ring or a 6-membered unsaturated ring.

2. The iridium complex of claim 1, wherein A1, A2, A3, A4 and A5 on a left side of formula (I) are respectively identical to A1, A2, A3, A4 and A5 on a right side of formula (I).

3. The iridium complex of claim 1, wherein at least one of A1, A2, A3, A4 or A5 on a left side of formula (I) is different from the corresponding A1, A2, A3, A4 or A5 on a right side of formula (I).

4. The iridium complex of claim 1, wherein at least one substituent on A1, A2, A3, A4 or A5 on a left side of formula (I) is different from a substituent at the corresponding position on the corresponding A1, A2, A3, A4 or A5 on a right side of formula (I).

5. The iridium complex of claim 1, represented by general formula (IA):

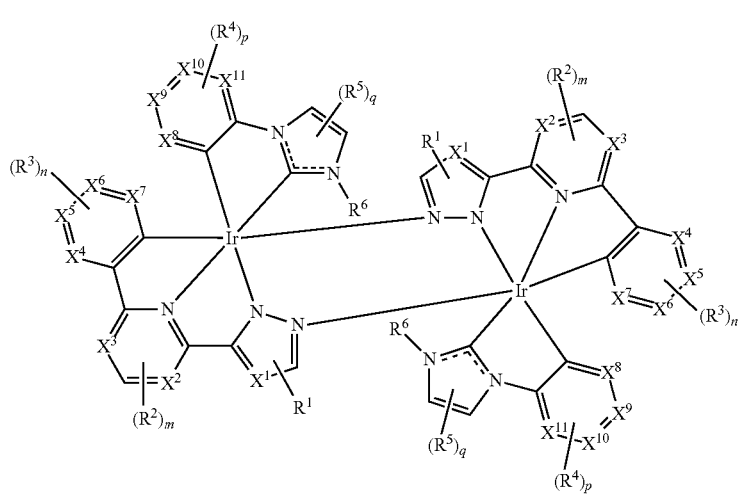

(IA)

wherein each $X^1$ to $X^{11}$ are each independently carbon or nitrogen;

each $R^1$ is independently hydrogen, substituted or unsubstituted $C_1$-$C_{12}$ alkyl, substituted or unsubstituted $C_6$-$C_{12}$ aryl, or —$C_fF_{2f+1}$, and f is an integer of 0 to 3;

each $R^2$, each $R^3$ and each $R^4$ are independently hydrogen, substituted or unsubstituted $C_1$-$C_{12}$ alkyl, substituted or unsubstituted $C_1$-$C_6$ alkoxyl, substituted or unsubstituted $C_6$-$C_{12}$ aryl, or —$C_fF_{2f+1}$, and f is an integer of 0 to 3;

m is an integer of 0 to 3;

n is an integer of 0 to 4;

p is an integer of 0 to 4;

each $R^5$ is independently hydrogen, substituted or unsubstituted $C_1$-$C_{12}$ alkyl, or substituted or unsubstituted $C_1$-$C_6$ alkoxy;

q is an integer of 1 to 2;

each $R^6$ is independently hydrogen, substituted or unsubstituted $C_1$-$C_{12}$ alkyl, or substituted or unsubstituted $C_6$-$C_{12}$ aryl;

when m is equal to or greater than 2, two or more $R^2$'s can joint to form a $C_3$-$C_8$ aromatic ring;

when n is equal to or greater than 2, two or more $R^3$'s can joint to form a $C_3$-$C_8$ aromatic ring;

when p is equal to or greater than 2, two or more $R^4$'s can joint to form a $C_3$-$C_8$ aromatic ring; and when q is equal to or greater than 2, two or more $R^5$'s can joint to form a $C_3$-$C_8$ aromatic ring.

6. The iridium complex of claim 5, having a structure represented by one of formula (IA-1) to formula (IA-50):

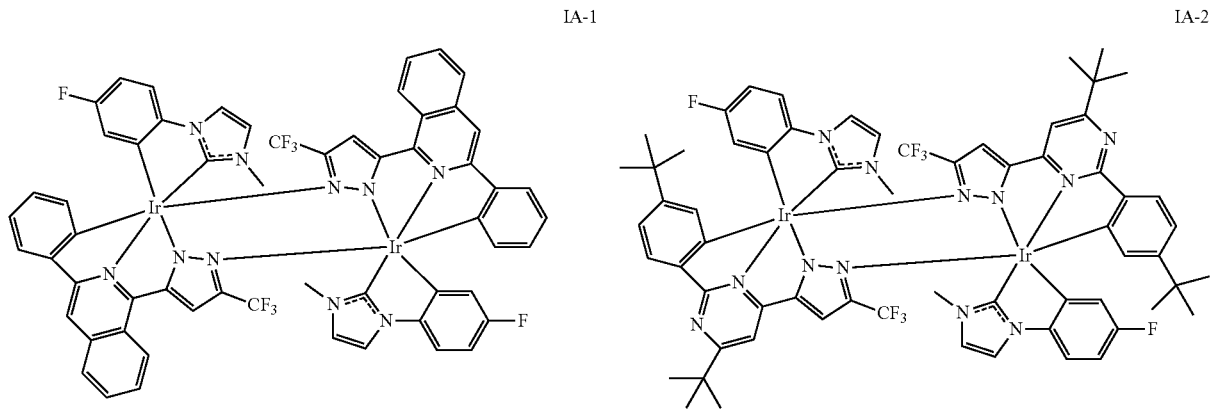

-continued
IA-3
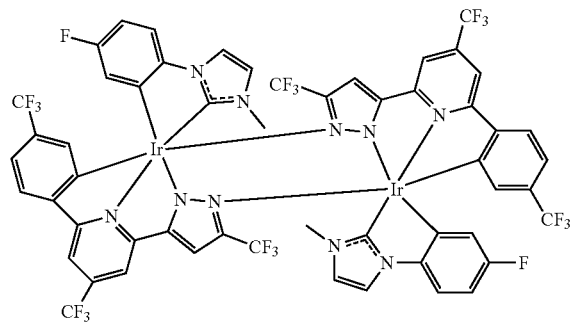
IA-4
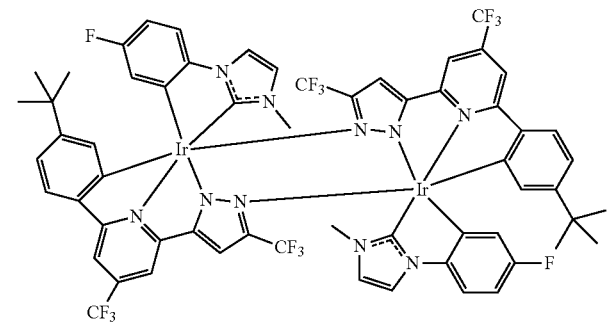
IA-5
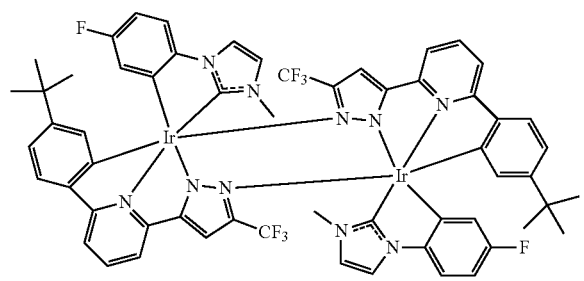
IA-6
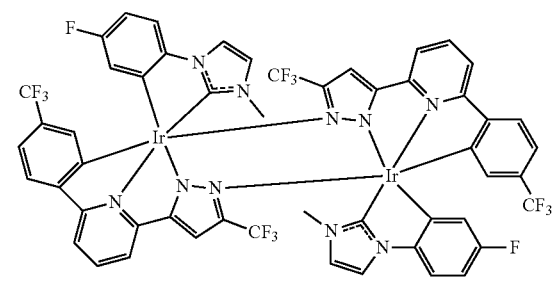
IA-7
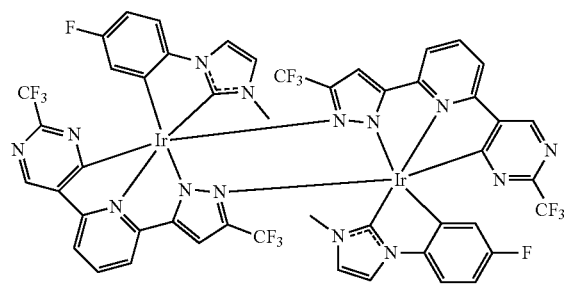
IA-8
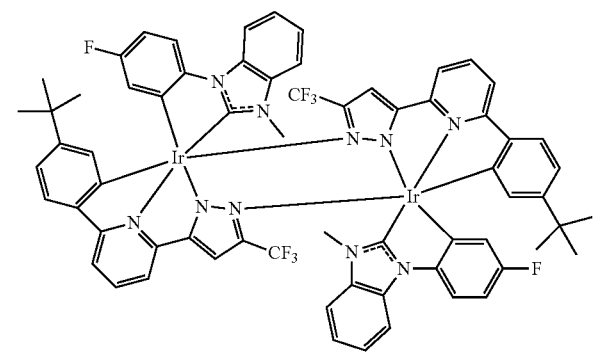
IA-9
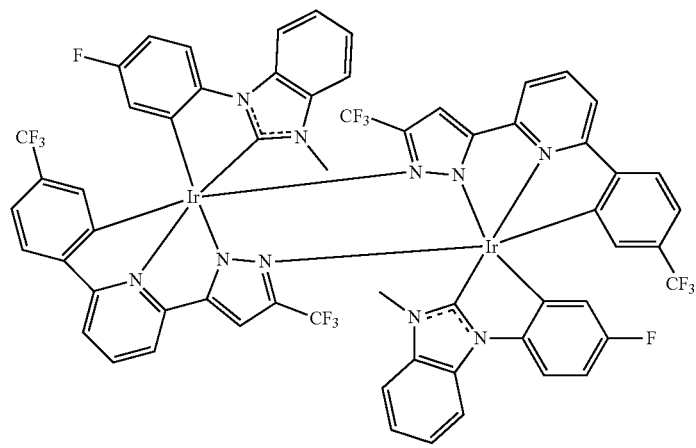

-continued
IA-10
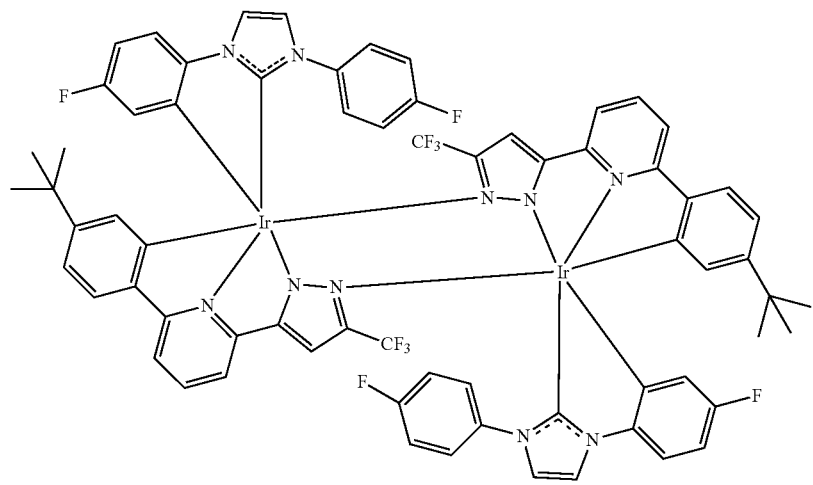
IA-11
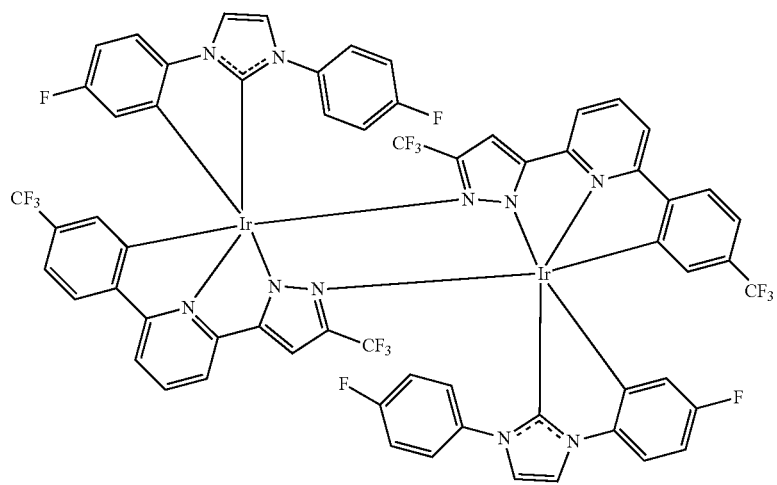
IA-12
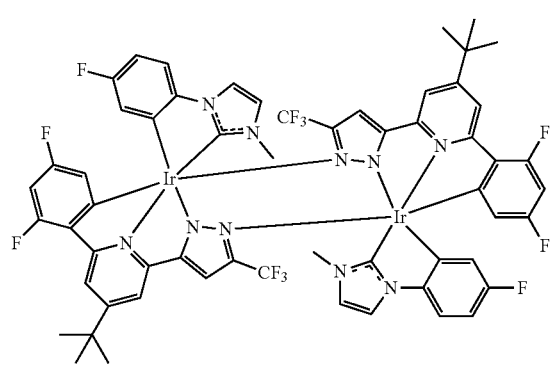
IA-13
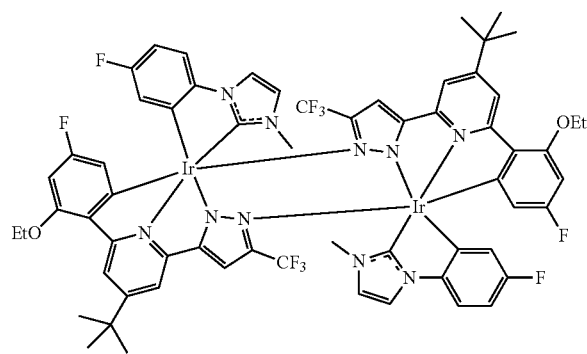

-continued
IA-14
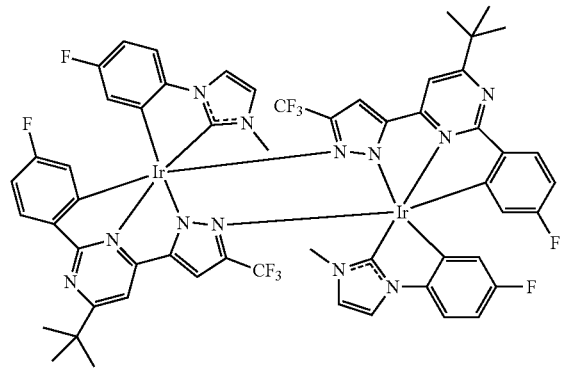
IA-15
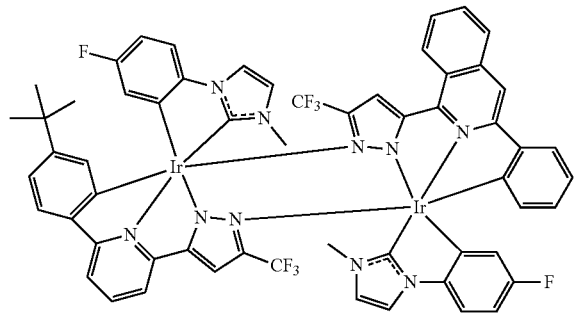
IA-16
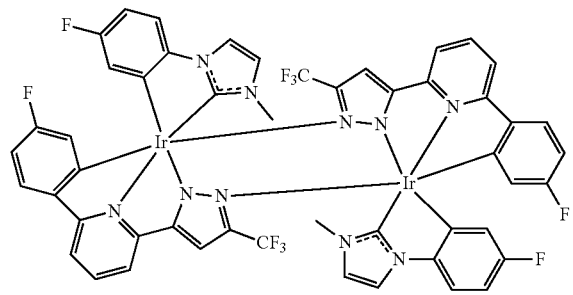
IA-17
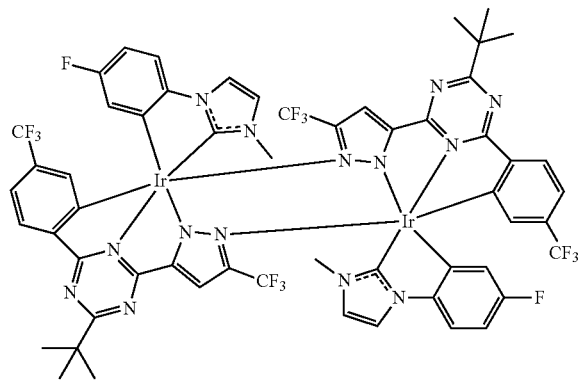
IA-18
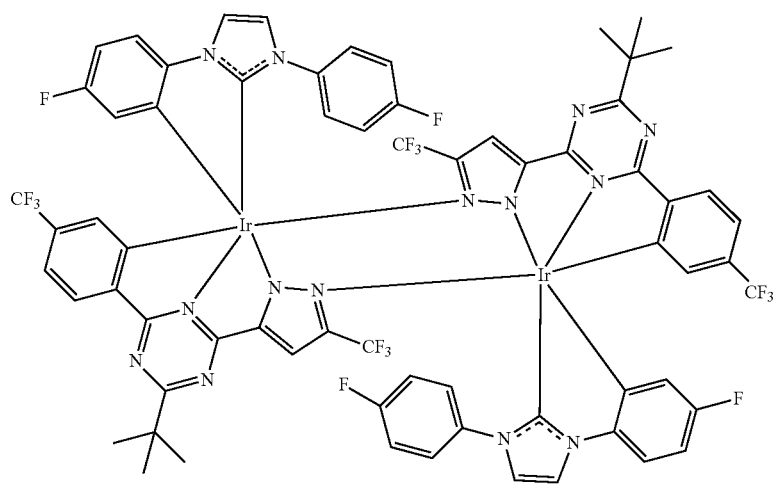

IA-19
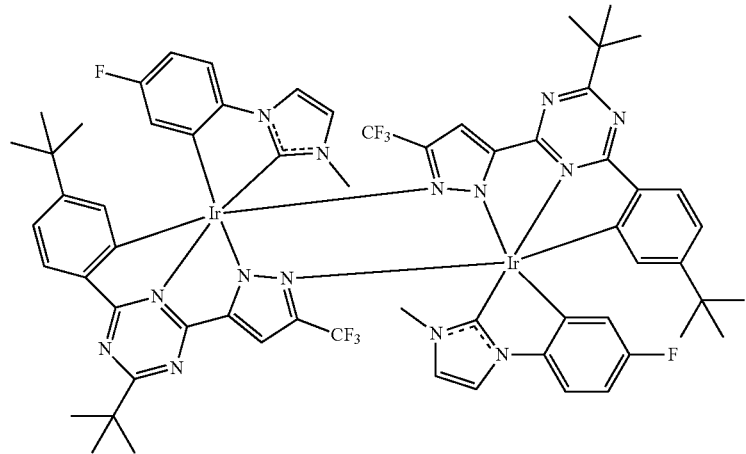
IA-20
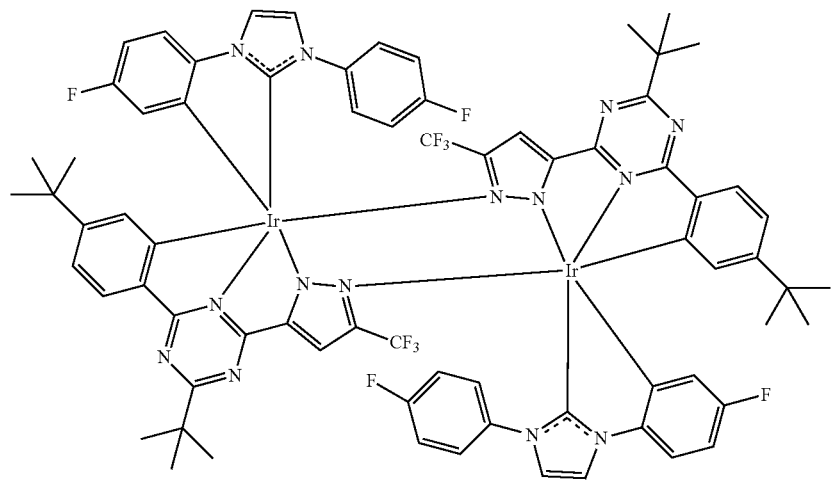
IA-21
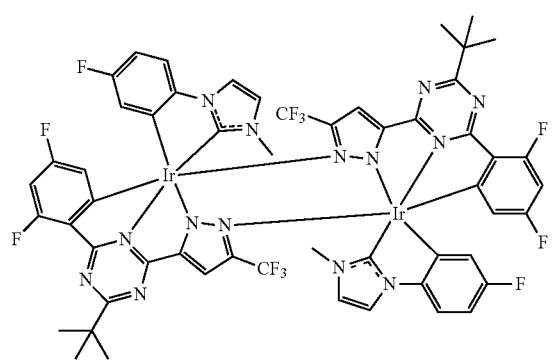
IA-22
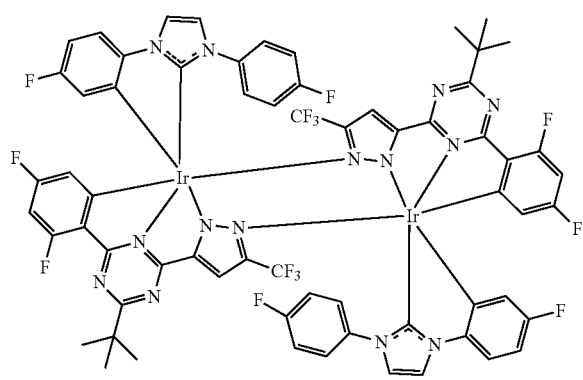

-continued
IA-23
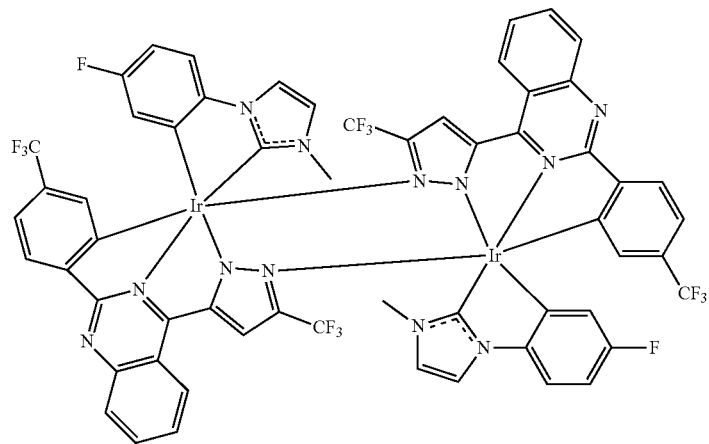
IA-24
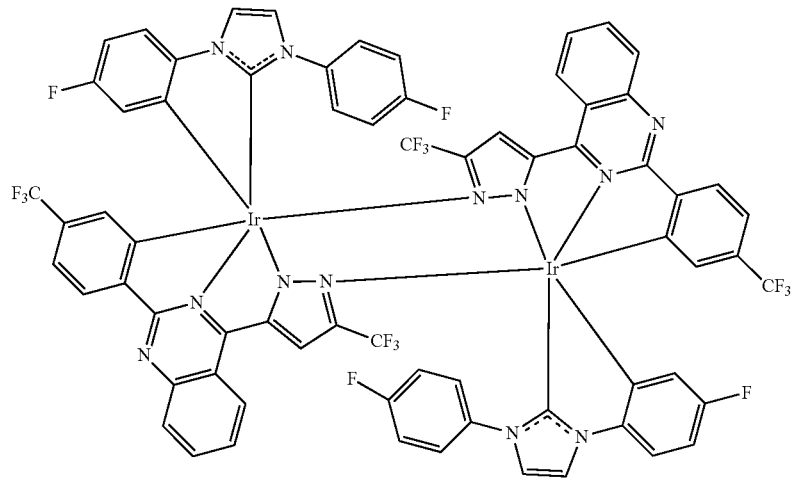
IA-25
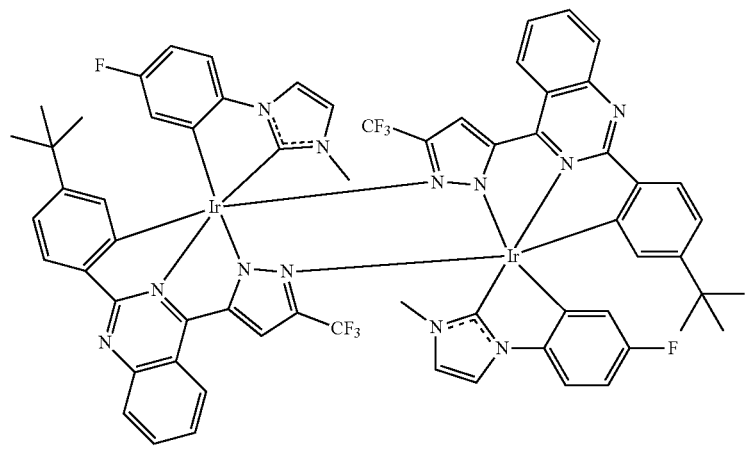

-continued
IA-26
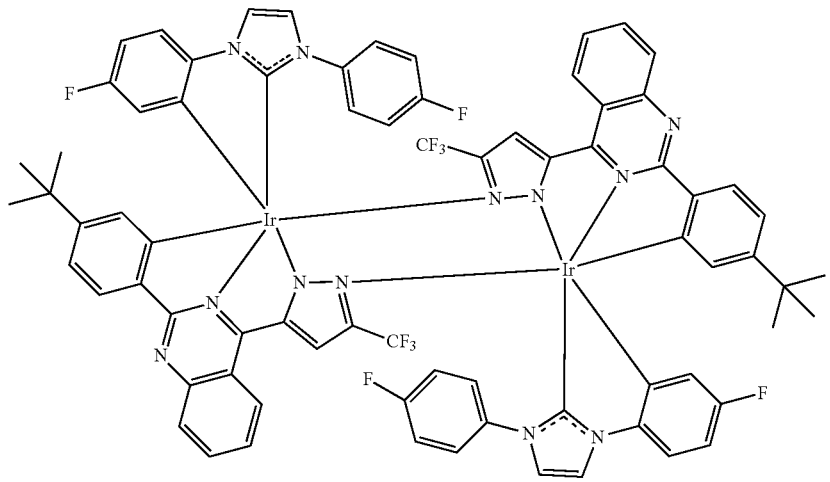
IA-27
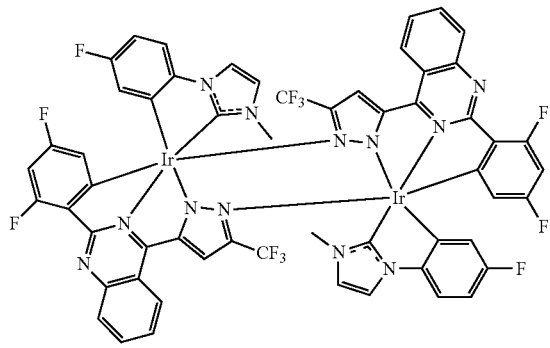
IA-28
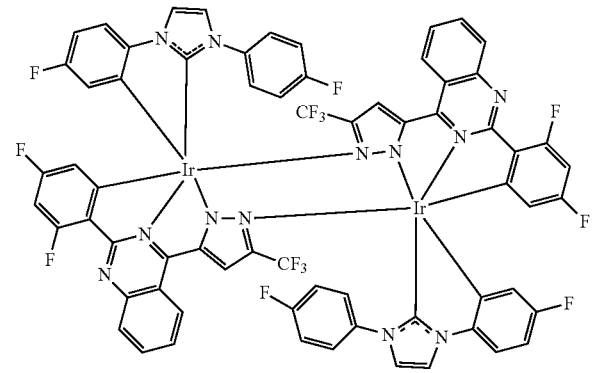
IA-29
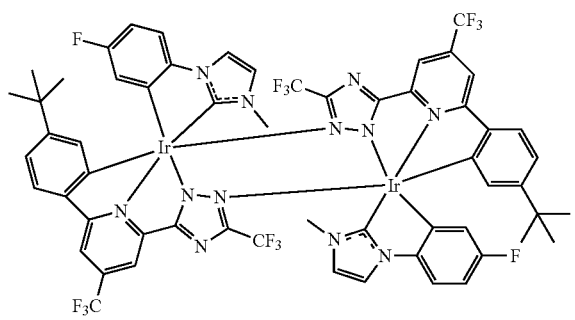
IA-30
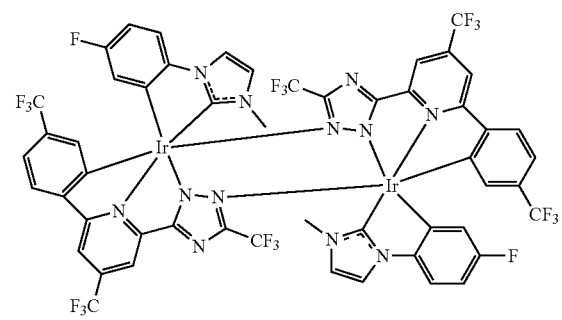
IA-31
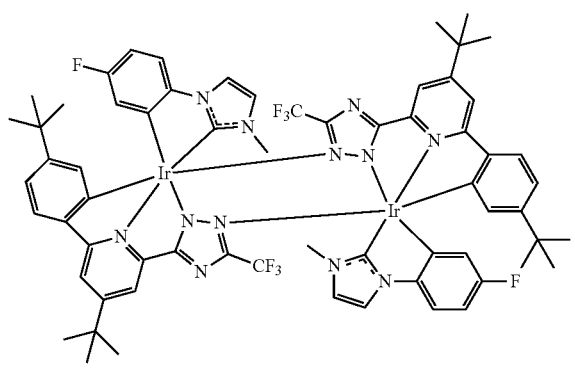
IA-32
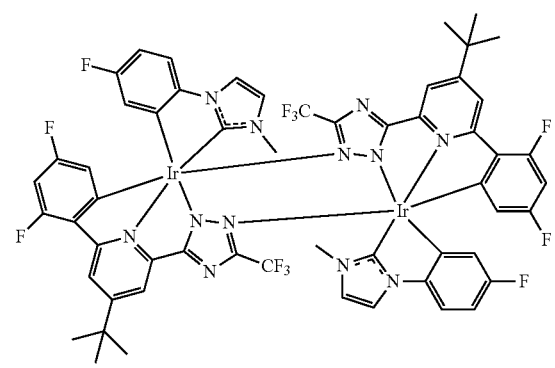

-continued
IA-33
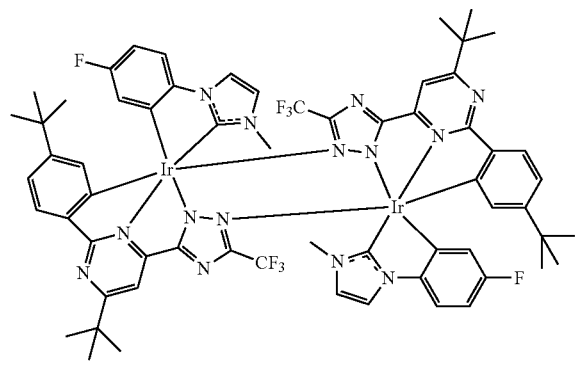
IA-34
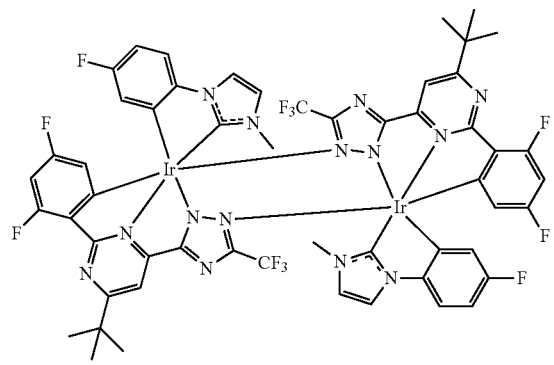
IA-35
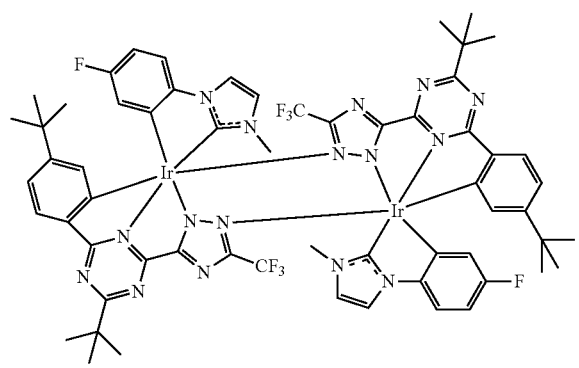
IA-36
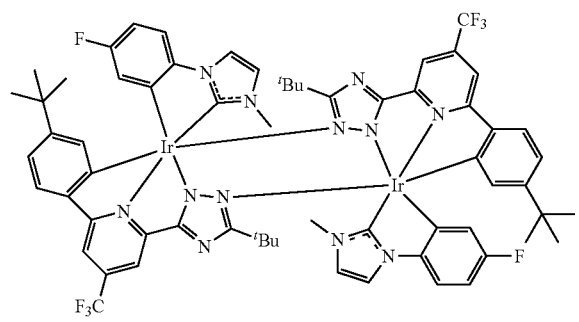
IA-37
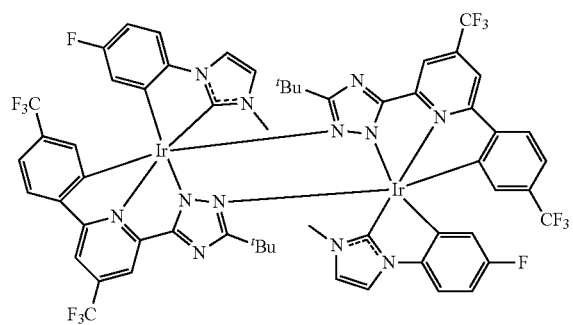
IA-38
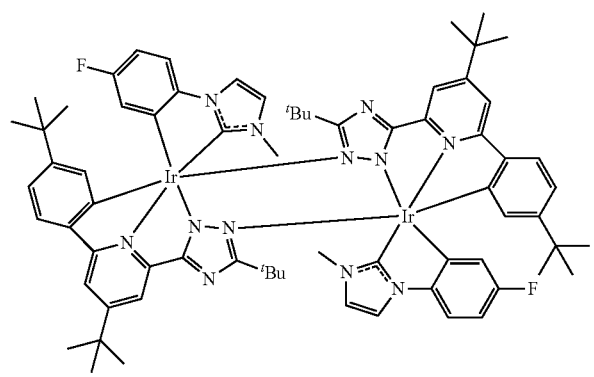
IA-39
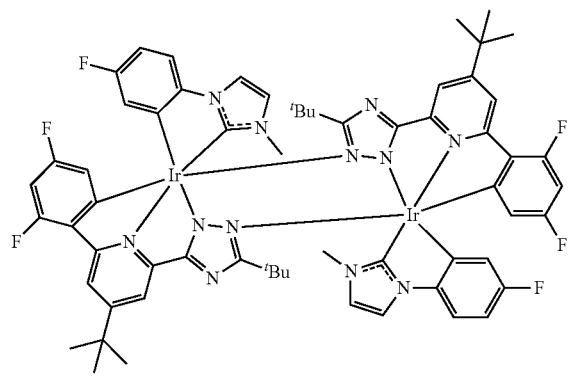
IA-40
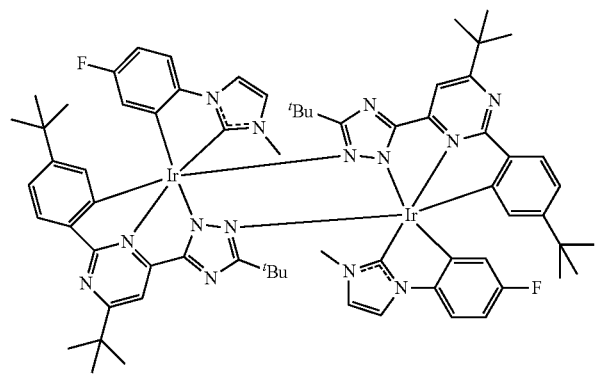

-continued
IA-41
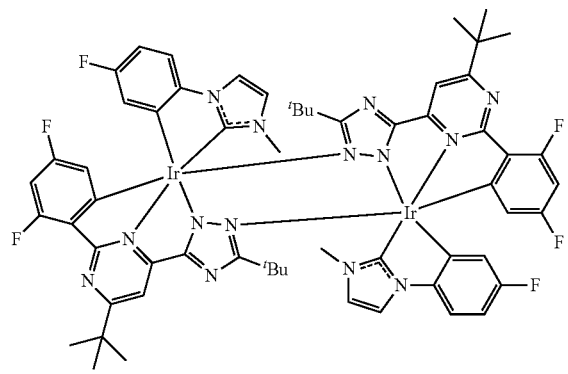
IA-42
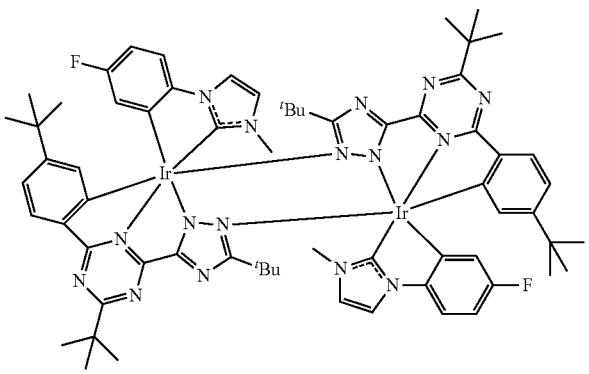
IA-43
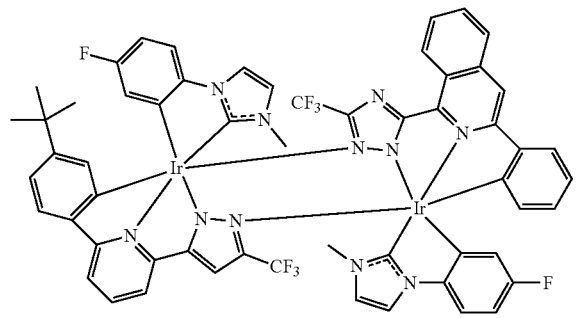
IA-44
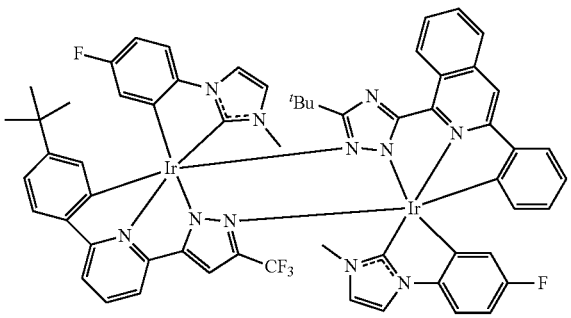
IA-45
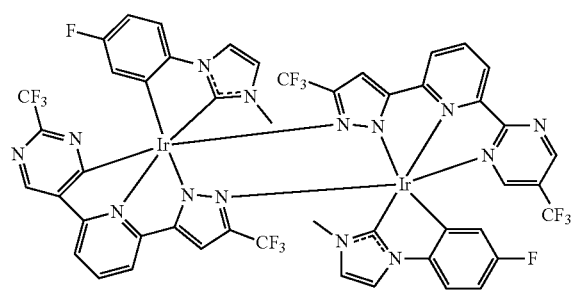
IA-46
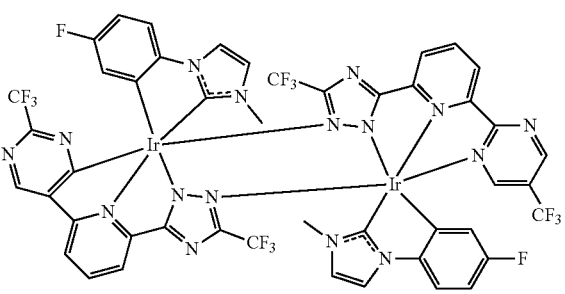
IA-47
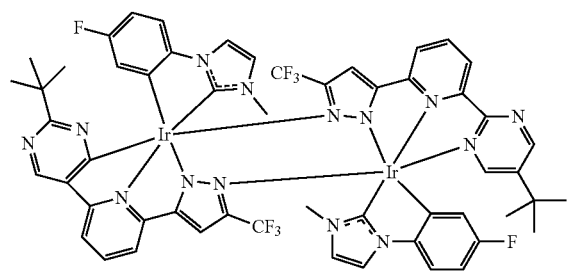
IA-48
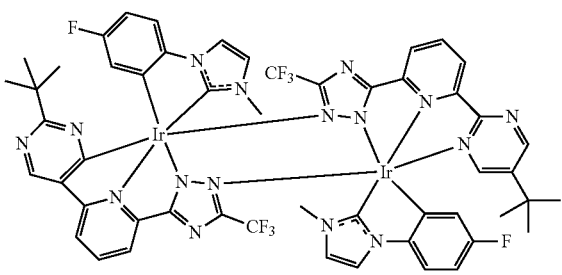

-continued
IA-49
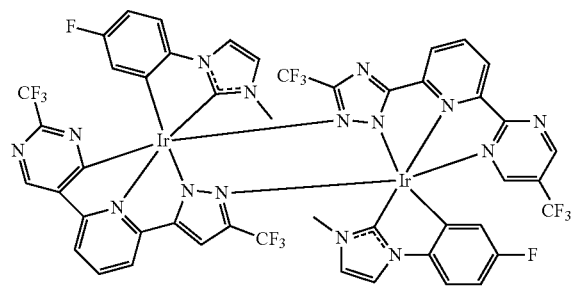
IA-50
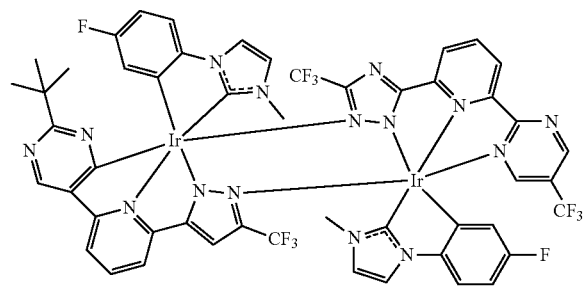
7. An organic light-emitting diode, comprising two electrodes and a light-emitting layer disposed between the two electrodes, wherein the light-emitting layer contains the iridium complex of claim 1.
* * * * *